United States Patent
Yoshida et al.

(10) Patent No.: US 7,354,775 B2
(45) Date of Patent: Apr. 8, 2008

(54) REAGENT FOR PARTIALLY LYSING A CELL MEMBRANE OF A RED BLOOD CELL, A REAGENT FOR DETECTING MALARIA INFECTED RED BLOOD CELLS, AND A SAMPLE ANALYZING METHOD FOR DETECTING MALARIA INFECTED RED BLOOD CELLS

(75) Inventors: Ayumu Yoshida, Kobe (JP); Kinya Uchihashi, Kakogawa (JP); Yuji Itose, Kako-gun (JP); Aya Konishi, Nishinomiya (JP); Hiromitsu Iizuka, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 11/390,298

(22) Filed: Mar. 28, 2006

(65) Prior Publication Data
US 2006/0223137 A1    Oct. 5, 2006

(30) Foreign Application Priority Data
Mar. 29, 2005 (JP) .............................. 2005-094885

(51) Int. Cl.
*G01N 33/555* (2006.01)
(52) U.S. Cl. ..................................... 436/522
(58) Field of Classification Search ................ None
See application file for complete search history.

(56) References Cited

U.S. PATENT DOCUMENTS 3,947,382 A * 3/1976 Kelly et al. ................ 510/499

5,470,751 A    11/1995 Sakata et al.
6,576,623 B1 * 6/2003 Nakanishi et al. ............ 514/63

FOREIGN PATENT DOCUMENTS

| EP | 0 613 003 A1 | 8/1994 |
| EP | 1 406 088 A2 | 4/2004 |
| JP | 11-75892 A | 3/1999 |
| JP | 2004-105027 A | 4/2004 |

OTHER PUBLICATIONS

Lambert et al. Journal of Applied Microbiology 2004;96:244-253.*
2 printout from web sites.*
Phikip H. Van, et al, "Flow Cytometric Screening of Blood Samples for Malaria Parasites", Cytometry, vol. 14, 1993, pp. 276-280.
Howard, R.J., et al, "*Plasmodium Infected Blood Cells Analyzed and Sorted by Flow Fluorometry With the DNA Binding Dye 33258 HOECHST*", vol. 27, No. 4, 1979, pp. 803-813, XP002392495.

* cited by examiner

*Primary Examiner*—Ralph Gitomer
*Assistant Examiner*—Bin Shen
(74) *Attorney, Agent, or Firm*—Sughrue Mion, PLLC

(57) ABSTRACT

A reagent for partially lysing a cell membrane of a red blood cell infected with a malaria parasite, comprising: a first surfactant which has predetermined lysing ability for the red blood cell membrane; and a second surfactant which has weaker lysing ability than that of the first surfactant; wherein the reagent has pH of 5 to 7 and osmotic pressure of 200 to 300 mOsm/kg·$H_2O$; and wherein the reagent partially lyses the malaria infected red blood cell membrane such that a malaria parasite is retained in the red blood cell and fluorescent dye passes through the cell membrane, is disclosed. A reagent for detecting malaria infected red blood cells, and a sample analyzing method for detecting malaria infected red blood cells, are also disclosed.

9 Claims, 21 Drawing Sheets

(a)

(b)

REAGENT FOR PARTIALLY LYSING A CELL MEMBRANE OF A RED BLOOD CELL, A REAGENT FOR DETECTING MALARIA INFECTED RED BLOOD CELLS, AND A SAMPLE ANALYZING METHOD FOR DETECTING MALARIA INFECTED RED BLOOD CELLS

FIELD OF THE INVENTION

The present invention relates a reagent for partially lysing a cell membrane of a red blood cell, a reagent for detecting malaria infected red blood cells, and a sample analyzing method for detecting malaria infected red blood cells.

BACKGROUND

Malaria is a parasitic infection distributed widely in the subtropical zone. Its pathogen is a malaria parasite classified as apicomplexa and is transmitted by an anopheles mosquito.

Malaria is classified into 4 types, that is, tropical malaria, tertian malaria, quartan malaria and ovale malaria, among which tropical malaria is particularly malignant, and unless its therapy is initiated within a few hours after onset, tropical malaria is accompanied by severe symptoms and complications, resulting frequently in death. Other malaria, on the other hand, is not so severe and rarely leads to death.

Accordingly, tropical malaria and other malaria are considerably different in respect of treatment method and medicine to be used. Symptoms of tropical malaria become rapidly worse, thus making immediate treatment necessary, and from the viewpoint of saving a patient, there are cases where administration of medicine is initiated when the patient is suspected of having tropical malaria before the final diagnosis is not established. Accordingly, there is a possibility of wrong diagnosis and the side effect of the medicine administered. Other malaria does not require such immediate treatment and can thus be treated by spending much time.

In the stage of clinical diagnosis, therefore, it is very important to discriminate tropical malaria from other malaria rapidly and accurately thereby determining a suitable therapeutic method. Accordingly, early diagnosis of malaria, particularly tropical malaria, is important.

In treatment of tropical malaria, the type of medicine administered, the amount of the medicine administered and the administration span are empirically judged and determined by a physician on the basis of infection ratio (ratio of the number of malaria infected red blood cells to the number of total red blood cells contained in blood of a predetermined volume). In consideration of treatment of tropical malaria, it is therefore necessary to discriminate tropical malaria from other malaria, and it is also important to know the malaria infection ratio in blood from the patient.

As a conventional method used in detecting malaria, there is a method which comprises preparing a smear of blood collected from a predetermined object, subjecting it to Giemsa staining and observing it under a microscope to detect malaria infected red blood cells, or a method which comprises counting red blood cells and infected red blood cells in a specific visual field and calculating the infection ratio.

However, the method by observation under a microscope is troublesome because of necessity for the steps of preparing, fixing, staining and drying a smear. Further, sophisticated skills are necessary for discriminating malaria infected red blood cells from malaria uninfected red blood cells and for judging whether the type of malaria with which the cells were infected is tropical malaria or other malaria. In addition, much time (usually 15 minutes or more for one patient) is necessary for observation under a microscope.

As a method of automatically detecting malaria infected red blood cells, a method which involves staining malaria infected red blood cells with a fluorescent dye and detecting the malaria infected red blood cells with a flow cytometer is also developed.

However, when a nucleic acid fluorescent dye is used as described in the prior art referred to in U.S. Pat. No. 5,470,751, there is a problem that not only malaria infected red blood cells but also reticulocytes are stained, so the two kinds of cells cannot be discriminated from each other. Staining of only malaria infected red blood cells with a specific fluorescent dye (Auramine O analogue) at low concentration is proposed in U.S. Pat. No. 5,470,751 supra. In this method, however, discrimination of malaria uninfected red blood cells from infected red blood cells is not made sufficiently evident.

On the other hand, P. H. Vianen et al. (P. H. Vianen et al., Cytometry; 14:276-280) disclose a method which comprises lysing red blood cells with a lysing agent containing a buffer agent, formaldehyde and diethylene glycol, to release malaria parasites from the malaria infected red blood cells, staining the malaria parasites with a dye Hoechst 33258, and detecting the parasites with a flow cytometer. In this method, the influence of malaria uninfected red blood cells and reticulocytes is negligible, but there is a problem that the lysing and staining procedures are troublesome to require dozens of minutes or more.

JP-A 11-75892 discloses a method which comprises releasing malaria parasites by hemolysis, rapidly staining the malaria parasites specifically with a nucleic acid-staining dye and, without centrifugal separation, detecting them with a flow cytometer. However, discrimination between tropical malaria and other malaria is conducted generally by observing the form of malaria parasites in malaria infected red blood cells, so the method of JP-A 11-75892 supra wherein red blood cells are lysed can judge whether the cells are infected with malaria or not, but cannot determine whether the malaria is tropical malaria or not.

JP-A 2004-105027 proposes a method of judging the type of malaria parasite with a flow cytometer by utilizing a difference in the amount of a nucleic acid-binding dye between tropical malaria and other malaria. This method is a method which comprises lysing red blood cells in a sample to release malaria parasites, detecting the intensity of fluorescence from the malaria parasites in the measurement sample, and judging the type of the malaria parasites on the basis of the frequency distribution of malaria parasites having fluorescence intensity in a predetermined range.

However, the method of detecting malaria parasites released by lysing red blood cells, used in the above-mentioned references, that is, JP-A 11-75892, JP-A 2004-105027, and P. H. Vianen et al., Cytometry, 14:276-280, cannot determine accurate infection ratio for the following reason.

FIG. 1 shows a life cycle of malaria parasites in red blood cells, wherein malaria parasites which upon blood sucking by an anopheles mosquito, enter into the living body are released as merozoites from hepatocytes into blood, to enter into red blood cells thereby initiating the life cycle in red blood cells. In the life cycle in red blood cells, the malaria parasite grows into a ring form, trophozoite and schizont in this order, and the schizont when divided into a plurality of metozoites breaks the infected red blood cell to release merozoites from the red blood cell, and the merozoites released into blood enter other red blood cells and re-initiate the life cycle in red blood cells. The malaria parasite grows by repeating this cycle and continues breaking red blood cells in blood.

The red blood cell into which the ring form enters includes not only a red blood cell into which one ring formenters (referred to hereinafter as "ring form (single)") but also a red blood cell into which two or more ring forms enter (referred to hereinafter as "ring form (multi)"). In the method of detecting parasites released by lysing red blood cells, however, a malaria parasite released from the ring form (single) and one of malaria parasites released from the ring form (multi) exhibit the same fluorescence intensity and thus cannot distinguished from each other. As a result, the ring form (multi) is regarded as a plurality of ring forms (single). There is also the case a schizont just before division may be regarded as being released from a plurality of red blood cells.

In the conventional method of observation under a microscope, on the other hand, the infection ratio is calculated assuming that the number of infected red blood cells is not affected by whether or not the ring forms (multi) exist and the schizont is in a matured stage just before division. Accordingly, the infection ratio obtained in the method which comprises lysing red blood cells and detecting released malaria parasites to determine the infection ratio on the basis of fluorescence intensity corresponding to the total amount of DNA in the malaria parasites does not agree with the infection ratio calculated in the conventional method of observation under a microscope. Particularly in the phenomenon in which a schizont just before division is divided by the influence of hemolysis into a plurality of metozoites or in tropical malaria where the proportion of a multi-infected red blood cell (that is, a red blood cell infected with 2 or 3 parasites) tends to be high, the infection ratio cannot be accurately grasped in the method directing attention to the frequency of released parasites obtained by lysing red blood cells. This means that in the medical field where a therapeutic method is selected and determined on the basis of the infection ratio calculated on the basis of the conventional method of observation under a microscope, tropical malaria can be judged, but selection of a suitable therapeutic method established up to now becomes difficult.

SUMMARY

The scope of the present invention is defined solely by the appended claims, and is not affected to any degree by the statements within this summary.

The object of the present invention is to detect malaria infected red blood cells in a blood sample easily, rapidly and accurately.

A first aspect of the present invention is a reagent for partially lysing a cell membrane of a red blood cell infected with a malaria parasite, comprising:
 a first surfactant which has predetermined lysing ability for the red blood cell membrane; and
 a second surfactant which has weaker lysing ability than that of the first surfactant;
  wherein the reagent has pH of 5 to 7 and osmotic pressure of 200 to 300 mOsm/kg·H$_2$O; and
  wherein the reagent partially lyses the malaria infected red blood cell membrane such that a malaria parasite is retained in the red blood cell and fluorescent dye passes through the cell membrane.

A second aspect of the present invention is a sample analyzing method for detecting malaria infected red blood cells, comprising:
 (a) preparing a measuring sample by lysing cell membranes of malaria infected red blood cells in a sample such that a malaria parasite is retained in the red blood cell and fluorescent dye, which is preferential for DNA over RNA, passes through the cell membrane, and by staining DNA of the malaria parasite by the fluorescent dye;
 (b) measuring fluorescent light and scattered light from the red blood cells in the measuring sample prepared in the step (a); and
 (c) detecting the malaria infected red blood cells based on the fluorescent light and the scattered light measured in the step (b)

A third aspect of the present invention is a sample analyzing method for detecting malaria infected red blood cells, comprising:
 (a) lysing cell membranes of malaria infected red blood cells in a sample such that a malaria parasite is held in the red blood cell and fluorescent dye, which is preferential for DNA over RNA, passes through the cell membrane;
 (b) staining DNA of the malaria parasite by the fluorescent dye;
 (c) exposing the sample which contains the red blood cells, to which the treatments in steps (a) and (b) have been applied, to irradiated light and obtaining optical information; and
 (d) detecting first red blood cells which have single ring form and/or second red blood cells which have two or more ring forms based on the optical information.

DETAILED DESCRIPTION OF THE PREFERRED EMBODIMENTS

Figure 1:
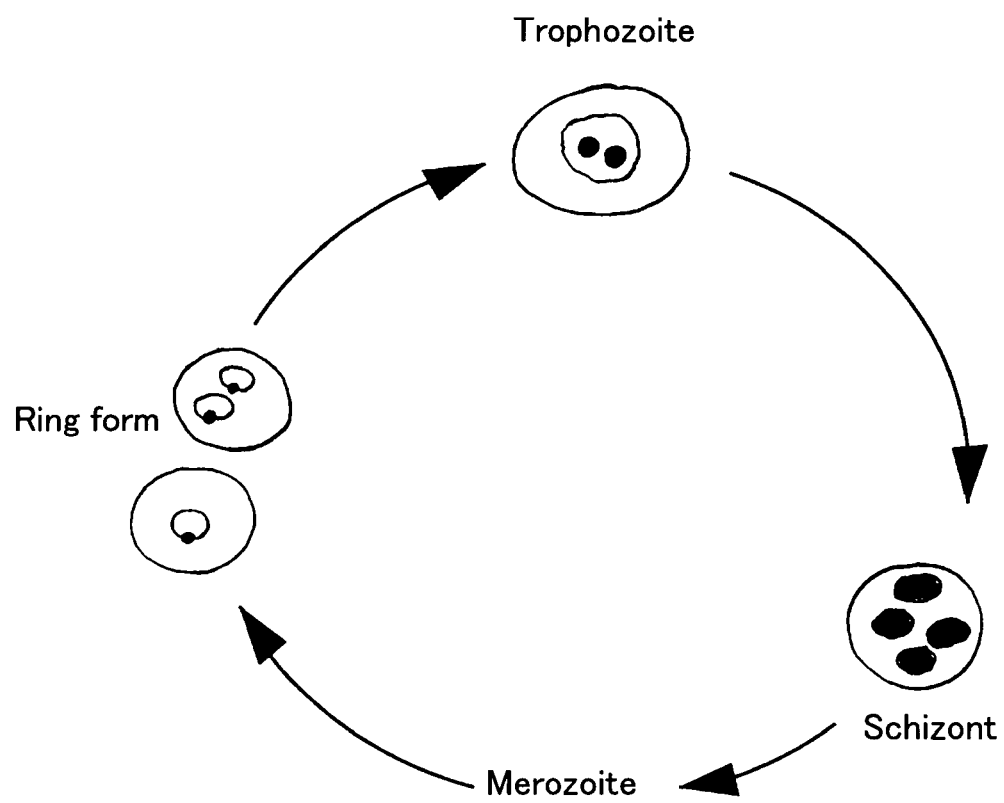
FIG. 1 is an illustration of a life cycle of malaria parasites in red blood cells.

The preferred embodiments of the present invention are described hereinafter with reference to the drawings.

A reagent, in this embodiments, for partially lysing a cell membrane of a red blood cell infected with a malaria parasite, may comprise: a first surfactant which has predetermined lysing ability for the red blood cell membrane; and a second surfactant which has weaker lysing ability than that of the first surfactant; wherein the reagent has pH of 5 to 7 and osmotic pressure of 200 to 300 mOsm/kg·$H_2O$; and wherein the reagent partially lyses the malaria infected red blood cell membrane such that a malaria parasite is retained in the red blood cell and fluorescent dye passes through the cell membrane.

The first and second surfactant maybe quaternary ammonium salts which have long chain alkyl groups.

The carbon number of the alkyl group of the second surfactant may be smaller than that of the alkyl group of the first surfactant.

The first surfactant may be stearyl trimethyl ammonium chloride, and the second surfactant may be lauryl trimethyl ammonium chloride.

The reagent may comprise a nonionic surfactant which substantially dose not have lysing ability to the red blood cell membrane.

The nonionic surfactant may be selected from the group consisting of polyoxyethylene sorbitan monoisostearate, polyoxyethylene sorbitan monooleate, polyoxyethylene hydrogenated castor oil, polyoxyethylene phytosterol, polyoxyethylene phytostanol, polyoxyethylene laurylether, polyoxyethylene oreylether, polyoxyethylene polyoxypropylene decyltetradecylether, polyoxyethylene polyoxypropylene cetylether, and polyoxyethylene monolaurate.

A reagent, in this embodiments, for detecting a malaria infected red blood cell may comprise the reagent for partially lysing a cell membrane of a red blood cell infected with a malaria parasite; and bisbenzimide type fluorescent dye which is preferential for DNA over RNA.

The bisbenzimide type fluorescent dye may have the following chemical formula.

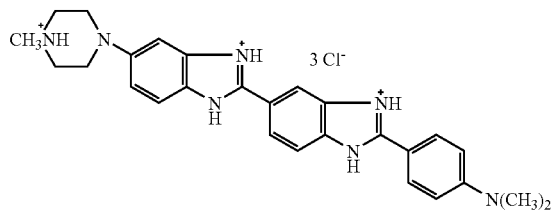

A sample analyzing method, in this embodiments, for detecting malaria infected red blood cells may comprise: (a) preparing a measuring sample by lysing cell membranes of malaria infected red blood cells in a sample such that a malaria parasite is retained in the red blood cell and fluorescent dye, which is preferential for DNA over RNA, passes through the cell membrane, and by staining DNA of the malaria parasite by the fluorescent dye; (b) measuring fluorescent light and scattered light from the red blood cells in the measuring sample prepared in the step (a); and (c) detecting the malaria infected red blood cells based on the fluorescent light and the scattered light measured in the step (b).

The step (b) may comprise (d) introducing the measuring sample in a flow cell; (e) exposing the measuring sample which flows in the flow cell to excitation light; and (f) detecting the fluorescent light and the scattered light from the red blood cells in the measuring sample.

The step (c) may comprise (g) making a scatter diagram based on fluorescent light intensity and scattered light intensity, and identifying a malaria infected red blood cell area for the malaria infected red blood cells on the scatter diagram.

The step (b) may comprise (d) introducing the measuring sample in a flow cell; (e) exposing the measuring sample which flows in the flow cell to excitation light; and (f) detecting the fluorescent light and the scattered light from the red blood cells in the measuring sample.

The step (c) may comprise (g) making a scatter diagram based on fluorescent light intensity and scattered light intensity, and identifying a malaria infected red blood cell area for the malaria infected red blood cells on the scatter diagram.

The step (c) may comprise detecting first malaria infected red blood cells and/or second malaria infected red blood cells based on fluorescent light and scattered light, the first malaria infected red blood cells having single ring form and the second malaria infected red blood cells having two or more ring forms.

The step (c) may comprise detecting and counting the malaria infected red blood cells based on fluorescent light and scattered light, and comprise obtaining a malaria infected ratio based on the malaria infected red blood cell count (M).

The step (c) may comprise detecting and counting white blood cells based on the fluorescent light and the scattered light, and the malaria infected ratio may be obtained by the following formula:

the malaria infected ratio $(\%) = K*(M*WBC)/(W*RBC)*100$;

wherein "WBC" represents a white blood cell concentration of the sample, "RBC" represents a red blood cell concentration of the sample, "W" represents a white blood cell count, and "K" represents a constant number.

The malaria infected ratio may be obtained by the following formula;

the malaria infected ratio $(\%) = K*M/(RBC*V)*100$;

wherein "RBC" represents a red blood cell concentration of the sample, "V" represents a volume of the sample used for preparing the measuring sample, and "K" represents a constant number.

The malaria infected ratio may be obtained by the following formula;

the malaria infected ratio $= M/(G+M)*100$;

wherein "G" represents a malaria non-infected red blood cell count.

In the step (a), the cell membranes of malaria infected red blood cells may be partially lysed by a reagent which comprises: a first surfactant which has predetermined lysing ability for the cell membrane of a red blood cell; and a second surfactant which has weaker lysing ability than that of the first surfactant.

A sample analyzing method, in this embodiments, for detecting malaria infected red blood cells may comprise: (a) lysing cell membranes of malaria infected red blood cells in a sample such that a malaria parasite is held in the red blood cell and fluorescent dye, which is preferential for DNA over RNA, passes through the cell membrane; (b) staining DNA of the malaria parasite by the fluorescent dye; (c) exposing the sample which contains the red blood cells, to which the treatments in steps (a) and (b) have been applied, to irradiated light and obtaining optical information; and (d) detecting first red blood cells which have single ring form and/or second red blood cells which have two or more ring forms based on the optical information.

The optical information may comprise first information about fluorescent light and second information about scattered light which are generated by exposing the sample to the irradiated light.

The step (d) may comprise (e) making a scatter diagram of fluorescent light intensity and scattered light intensity based on the first and second information, and identifying a first area for the first red blood cells and/or a second area for the second red blood cells on the scatter diagram.

The step (d) may further comprise (f) counting the first red blood cells and the second red blood cells.

[Reagent for Partially Lysing a Red Blood Cell Membrane]

Now, the reagent for partially lysing a red blood cell membrane, which is preferable for the method of detecting malaria infected red blood cells in this embodiment, is described in detail.

The reagent for partially lysing a red blood cell membrane in this embodiment is a reagent which lyses a red blood cell membrane to such an extent that the shape of a red blood cell is maintained but a fluorescent dye can penetrate into it, and the reagent contains a surfactant for lysing a red blood cell membrane. The red blood cell may be deformed insofar as the malaria parasite can be retained in the cell. The reagent may contain one kind of surfactant but preferably contains two or more surfactants different in the ability to lyse a red blood cell membrane in order to attain higher performance. The reagent for partially lysing a red blood cell membrane in this embodiment preferably has pH 5.0 to 7.0 and an osmotic pressure of 200 to 300 mOsm/kg.

As the surfactant, it is possible to use an anionic surfactant, a nonionic surfactant or a cationic surfactant, among which the cationic surfactant is preferably used.

As the cationic surfactant, it is possible to use, specifically, octyl trimethyl ammonium bromide (OTAB), decyl trimethyl ammonium bromide (DTAB), lauryl trimethyl ammonium chloride (LTAC), myristyl trimethyl ammonium bromide (MTAB), cetyl pyridinium chloride (CPC), stearyl trimethyl ammonium chloride (STAC) etc. A combination of two or more surfactants different in the ability to lyse a red blood cell membrane is preferably selected from these surfactants.

The ability to lyse a red blood cell membrane depends mainly on the number of carbon atoms contained in the surfactant. Specifically, as the number of carbon atoms is increased or as a carbon chain of a linear alkyl group moiety of a quaternary ammonium salt when used as a surfactant is increased, the lysing power is increased but the surfactant is easily solidified at ordinary temperatures. Accordingly, a surfactant having a smaller number of carbon atoms is used as a solubilizer thereby increasing the solubility, in a solvent, of the reagent for partially lysing a red blood cell membrane and regulating the influence thereof on a red blood cell membrane.

The combination of surfactants and the concentration thereof in the reagent may be selected such that by specifically combining surfactants, a red blood membrane is lysed to such a degree that a fluorescent dye can penetrate into a red blood cell and simultaneously the shape of the red blood cell can be maintained. For example, when a combination of STAC containing 21 carbon atoms (the number of carbon atoms in the longest alkyl group: 18) and LTAC containing 15 carbon atoms (the number of carbon atoms in the longest alkyl group: 12) is selected, a mixture of 40 to 600 ppm STAC and 500 to 1400 ppm LTAC is preferably used.

Further, a nonionic surfactant substantially not lysing a red blood cell membrane is preferably added. Malaria infected red blood cells can be classified more accurately depending on the growth stage of the malaria parasite.

As the nonionic surfactant, it is preferable to use polyoxyethylene sorbitan fatty acid esters such as polyoxyethylene (20) sorbitan monoisostearate and polyoxyethylene (20) sorbitan monooleate, polyoxyethylene castor oils/hydrogenated castor oils such as polyoxyethylene (30) hydrogenated castor oil and polyoxyethylene (50) hydrogenated castor oil, polyoxyethylene phytosterols such as polyoxyethylene (20) phytosterol and polyoxyethylene (25) phytostanol, polyoxyethylene alkyl ethers such as polyoxyethylene (21) lauryl ether, polyoxyethylene (16) oreyl ether and polyoxyethylene (20) oreyl ether, polyoxyethylene polyoxypropylene alkyl ethers such as polyoxyethylene (20) polyoxypropylene (6) decyl tetradecyl ether andpolyoxyethylene (20) polyoxypropylene (8) cetyl ether, and polyoxyethylene fatty acid esters such as polyoxyethylene (10) monolaurate.

The reagent for partially lysing a red blood cell membrane in this embodiment can contain a buffer agent for maintaining a constant pH value. The type of the buffer agent is not limited insofar as the buffer agent can maintain a pH value suitable for stably carrying out the reaction in this embodiment. The pH value is preferably in the range of 5.0 to 7.0.

As the buffer agent, use can be made of citric acid, phosphoric acid, succinic acid, tricinetc. For pH adjustment, hydrochloric acid, sodium hydroxide or the like may be added as a pH adjusting agent.

An osmotic pressure regulating agent is preferably contained to keep a constant osmotic pressure of the reagent. The osmotic pressure is preferably 200 to 300 mOsm/kg·$H_2O$. When the osmotic pressure is less than 200 mOsm/kg, red blood cells tend to be swollen by incorporation of the reagent or liquid components in blood, which can result in hypotonic lysis of the red blood cells. When the osmotic pressure is higher than 300 mOsm/kg, a fluorescent dye for detecting malaria infected red blood cells, which will be described later, hardly penetrates into a red blood cell, which can lead to a structural change in the red blood cell by shrinkage.

Alkali metal halides such as sodium chloride, alkaline earth halides such as magnesium chloride, metal carboxylates such as propionate, and sugars such as glucose and mannose are preferably used as the osmotic pressure regulating agent.

If necessary, the reagent may contain preservatives such as sodium 2-pyridylthio-1-oxide and β-phenethyl alcohol.

For regulating the concentration, the reagent may be diluted with purified water, ethanol etc. in such a range that the pH and osmotic pressure are not affected.

[Detection Reagent]

The reagent for detection of malaria infected blood cells in this embodiment comprises the above-mentioned reagent for partially lysing a red blood cell membrane in this embodiment and a DNA-selective fluorescent dye, preferably a DNA-selective bisbenzimide type fluorescent dye.

The DNA-selective fluorescent dye is a fluorescent dye staining preferentially DNA over RNA, and the DNA-selective bisbenzimide type fluorescent dye is a dye having a bisimide-based skeleton.

As the dye, a dye having the following structure (for example, Hoechst 34580 available from Invitrogen Corporation) is preferably used.

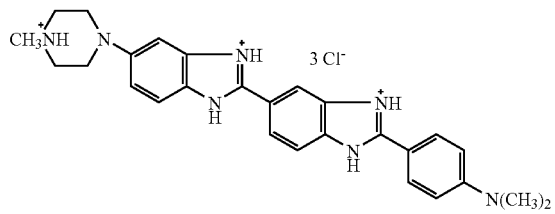

The DNA-selective bisbenzimide type fluorescent dye includes Hoechst 33258 and Hoechst 33342 in addition to the above-mentioned dye. These dyes are different in side chain from Hoechst 34580, and can be excited at blue wavelength (405 nm).

A red blood cell does not have a nucleus and is thus not stained with the DNA-selective fluorescent dye. In a malaria infected red blood cell, on the other hand, DNA in a malaria parasite having entered the red blood cell is stained. Accordingly, the infected red blood cells are stained with the DNA-selective fluorescent dye, but the uninfected red blood cells are not stained so that on the basis of a difference in fluorescence intensity on a scattergram obtained by a flow cytometer as described later, the two kinds of cells can be discriminated from each other.

Reticulocytes wherein RNA remains are also stained with the conventionally used nucleic acid fluorescent dye, thus permitting dots corresponding to the reticulocytes to appear in a region where the infected red blood cells appear in the scattergram, and as a result, the reticulocytes are contained in the region where the infected red blood cells appear. Reticulocytes occur usually in about 1% of red blood cells, and the infection ratio is also usually about 1%, so the reticulocytes are mistaken for infected red blood cells, thus causing a reduction in detection sensitivity and a reduction in accuracy in calculation of the infection ratio.

On the other hand, the detection reagent in this embodiment uses the fluorescent dye staining DNA preferentially over RNA, thus permitting reticulocytes to appear in the region where normal red blood cells appear in the scattergram, and therefore the reduction in accuracy of the infection ratio attributable to reticulocytes can be prevented.

The detection reagent in this embodiment may be contained either in a reagent kit of one pack type containing the DNA-selective fluorescent dye and the reagent for partially lysing a red blood cell membrane or in a reagent kit of two-pack type wherein the DNA-selective fluorescent dye and the reagent for partially lysing a red blood cell membrane are contained in separate containers respectively and mixed at use. In this case, the DNA-selective fluorescent dye may contain an alcohol such as ethylene glycol, purified water or a buffer as a solvent.

[Method of Detecting Malaria Parasite-infected Red Blood Cells]

The method of detecting malaria parasite-infected red blood cells in this embodiment comprises the steps of mixing a whole blood sample collected from a predetermined object, with the reagent for detecting malaria infected red blood cells in the embodiment, to prepare a measurement sample; introducing the measurement sample into a flow cell of a flow cytometer; irradiating the measurement sample flowing through the flow cell with an excitation light exciting a fluorescent dye contained in the reagent for detecting malaria infected red blood cells; detecting a scattered light and fluorescence emitted form the cells; preparing a scattergram of the scattered light intensity and fluorescence intensity on two axes; and specifying a region of malaria uninfected red blood cells and a region of malaria infected red blood cells on the scattergram.

First, a whole blood sample collected from a predetermined object is mixed with the above-described reagent for detecting malaria infected red blood cells in the embodiment, to prepare a measurement sample. The measurement sample is prepared by mixing the whole blood sample with the detection reagent and then incubating the mixture usually for example for 40 seconds. During this incubation, cells having DNA in blood are stained. Specifically, white blood cells, red blood cells into which malaria parasites entered, that is, infected red blood cells, are stained.

The infected red blood cell consists of a ring form, a trophozoite or a schizont shown in the life cycle of malaria parasites in FIG. 1. The ring form-containing infected red blood cell occurs as a ring form (single) wherein one malaria parasite enters into one red blood cell or as a ring form (multi) wherein two or more malaria parasites enter into one red blood cell. The red blood cells containing malaria parasites having such life cycle in red blood cells have a different total amount of DNA depending on the growth stage of the malaria parasite, thus exhibiting different fluorescence intensity depending on the growth stage. The ring form (single) and ring form (multi) are also different in respect of the total amount of DNA, thus showing fluorescence intensity different from each other.

Figure 2:
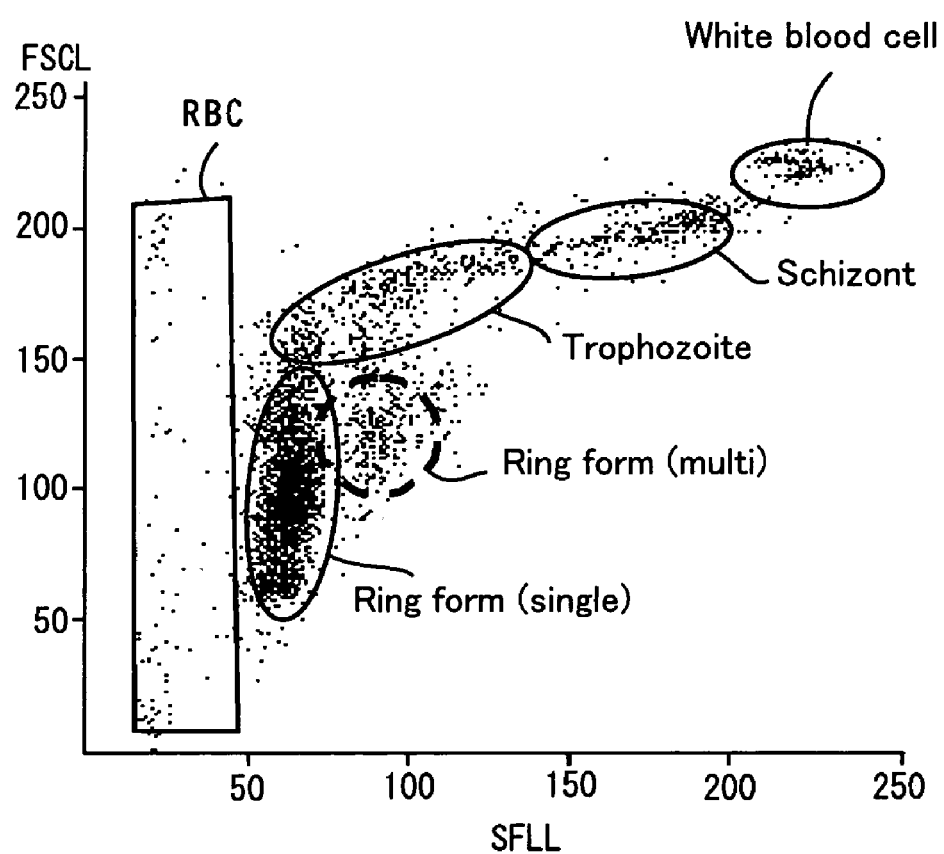
FIG. 2 is one example of the scattergram obtained by detecting malaria infected blood in the detection method of this embodiment.

Accordingly, the measurement sample containing a blood sample of tropical malaria is introduced into a flow cell, then the measurement sample flowing through the flow cell is irradiated with an excitation light exciting a fluorescent dye contained in the detection reagent, to detect the scattered light and fluorescence emitted from the measurement sample, and a scattergram having the scattered light intensity (ordinate) and the fluorescence intensity (abscissa) is prepared as shown in FIG. 2.

As shown in FIG. 2, the malaria uninfected red blood cells appear in a region of low fluorescence intensity, and as the malaria parasite grows into a ring form, trophozoite and schizont in this order, the malaria infected red blood cells appear in a region of higher fluorescence intensity and further in a region of greater size (higher scattered light intensity). With respect to the ring form, the ring form (multi) appears in a region of higher fluorescence intensity than that of the ring form (single), although the two ring forms appear in a region of the same size (the same scattered light intensity). The white blood cells appear in a region of higher fluorescence intensity and higher scattered light intensity because of their size and amount of DNA.

For specifying cells present in these regions, the scattergram is divided with a gate into each region. Whether a measurement sample is infected with malaria or not can be judged by measuring it with a flow cytometer and examining whether dots are present in the gate region of infected red blood cells or not in the obtained 2-dimensional scattergram.

When there are many dots present in the ring form (multi) in the gate region of infected red blood cells, the cells can be judged to be those infected with tropical malaria. This is based on the empirically known fact that tropical malaria tends to exhibit more ring forms (multi) than in other malaria.

Further, the infection ratio can be calculated by counting the number of dots present in the gate region of infected red blood cells, in the gate region of uninfected red blood cells depending on the method of calculating the infection ratio as described later, and in the gate region of white blood cells.

In the method of detecting malaria infected red blood cells in this embodiment, the detection is not based on malaria parasites released by lysing infected red blood cells, and the infected red blood cells maintaining their form are examined as such by a flow cytometer so that in the resulting scattergram, the growth stage of malaria can be grasped. Accordingly, the detection does not depend on the growth state or number of parasites with which the cells were infected, and each of the infected red blood cells is counted as one, and thus the infection ratio comparable with observation under a microscope can be determined.

[Method of Calculating the Infection Ratio]

The infection ratio is determined according to any of the following methods A to C.

Method A: Method of Utilizing the Ratio of White Blood Cell Concentration to Red Blood Cell Concentration Method A is a method which involves previously measuring the red blood cell concentration RBC and white blood cell concentration WBC of a sample and utilizing their ratio to determine the infection ratio on the basis of a scattergram prepared with a flow cytometer.

First, an objective sample is measured with a hemocytometer (existing cytometer, for example XE-2100 manufactured by Sysmex Corporation) to determine white blood cell concentration WBC (cells/µL) and red blood cell concentration RBC (cells/µL).

Dots in each cell region are counted in the scattergram (FIG. 3) where each cell region is divided with each gate in this embodiment, to determine white blood cell particle count (number of dots in W1 gate) W and malaria infected red blood cell count (number of dots in M1 gate region) M.

From the WBC/RBC ratio and white blood cell count W determined above, the number of red blood cells x contained in the measurement sample is determined according to the following formula (1):

$$x=(W \times RBC)/WBC \qquad (1)$$

From the red blood cell count x and the infected red blood cell count M determined above, the infection ratio ("Ratio") is calculated according to formula (2) below. In the formula (2), K is a correction constant determined in consideration of loss etc. in the measuring apparatus.

$$\text{Ratio}=K \times M/x \times 100 \qquad (2)$$

The infection ratio can be determined from the formulae 1 and 2 or directly from the following formula (3):

$$\text{Ratio}=K \times (M \times WBC)/(W \times RBC) \times 100 \qquad (3)$$

Similarly, the numbers of red blood cells containing malaria parasites in the predetermined growth stages, that is, ring form (single) count (number of dots in R1 gate) R1, ring form (multi) count (number of dots in R2 gate) R2, trophozoite-containing red blood cell count (number of dots in T gate) T, and schizont-containing red blood cell count (number of dots in S gate) S can be counted from the scattergram to determine the infection ratio in each growth stage in red blood cells.

Mr: percentage (%) of ring form-containing red blood cells in malaria infected RBC $$Mr=(R1+R2)/M \times 100$$

Mt: percentage (%) of trophozoite-containing red blood cells in malaria infected RBC $$Mt=T/M \times 100$$

Ms: percentage (%) of schizont-containing red blood cells in malaria infected RBC $$Ms=S/M \times 100$$

The ratio Mrm (%) of the ring form (multi) in ring form-containing red blood cells (R1+R2) can be calculated from the following formula (4):

$$Mrm=R2/(R1+R2) \times 100 \qquad (4)$$

Method B: Absolute Quantification Method

Figure 3:
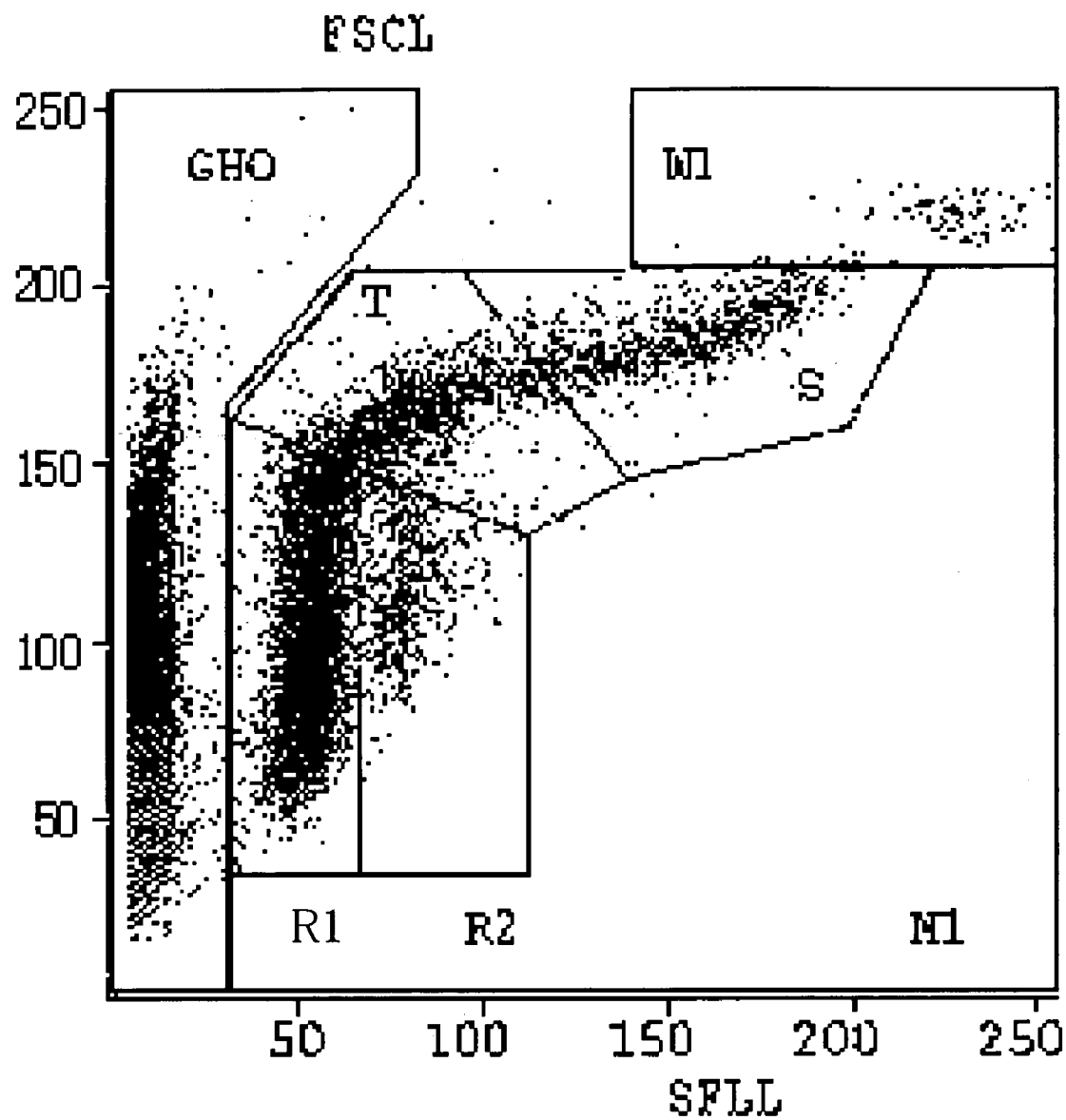
FIG. 3 is a scattergram showing the method of calculating the infection ratio.

Method B is a method wherein the red blood cell concentration RBC of a sample is previously measured, and from the volume of the sample used in preparing a measurement sample, the number of red blood cells contained in the measurement sample is calculated, and the ratio to the number of infected red blood cells calculated from the scattergram in FIG. 3 is determined.

The red blood cell concentration RBC is measured in the same manner as in method A, and on the basis of the scattergram in this embodiment and the specified measurement regions, the infected red blood cell count M is determined, and from the volume V (µL) of the sample used in preparing the measurement sample, the infection ratio Ratio is determined from the following equation (5):

$$\text{Ratio}=K \times M/(RBC \times V) \times 100 \qquad (5)$$

When the infection ratio in each growth stage is determined, the numbers of red blood cells containing malaria parasites in the predetermined growth stages, that is, ring form (single) count R1, ring form (multi) count R2, trophozoite-containing red blood cell count T, and schizont-containing red blood cell count S can be calculated from the scattergram in the same way as in the Method A to determine the infection ratio in each growth stage on the basis of the formula determining the infection ratio in each growth stage shown in the Method A. The ratio Mrm (%) of the ring form (multi) in the ring form-containing red blood cells can also be determined similarly according to the formula (4) above.

This method is advantageous over method A in that the white blood cell concentration may not be measured, but the amount of the sample used in preparing a measurement sample should be accurately measured.

Method C: Red Blood Cell Counting Method

Method C is a method which involves simultaneously counting uninfected red blood cells and infected red blood cells in a measurement sample and calculating the infection ratio therefrom.

From the scattergram in FIG. 3, the uninfected red blood cell count (number of dots in GHO gate region) G and the infected red blood cell count (number of dots in M1 gate) M are determined, and the malaria infection ratio Ratio is determined according to the following formula (6):

$$\text{Ratio}=M/(G+M)\times 100 \qquad (6)$$

When the infection ratio in each growth stage is determined, dots in each growth stage are counted in the same way as in the Method A and the infection ratio is calculated according to the formula in Method A. The ratio Mrm (%) of the ring form (multi) in the ring form-containing red blood cells can also be determined similarly according to the formula (4) above.

[Flow Cytometer]

The flow cytometer used in the detection method in this embodiment is not particularly limited, and it is possible to use, for example, an apparatus disclosed in JP-A 2004-10502, that is, an apparatus including a flow cell for introducing a measurement sample, and a light source for irradiating, with an excitation light, cells in a measurement sample flowing through the flow cell; a first detector for detecting the intensity of scattered light emitted from the cells irradiated with an excitation light; a second detector for detecting the intensity of florescence light emitted from the cells irradiated with an excitation light; and an analyzing unit for forming a scattergram with scattered light intensity and fluorescence intensity on two axes, to specify and calculate a region of malaria uninfected red blood cells and a region of infected red blood cells on the scattergram.

Figure 4:
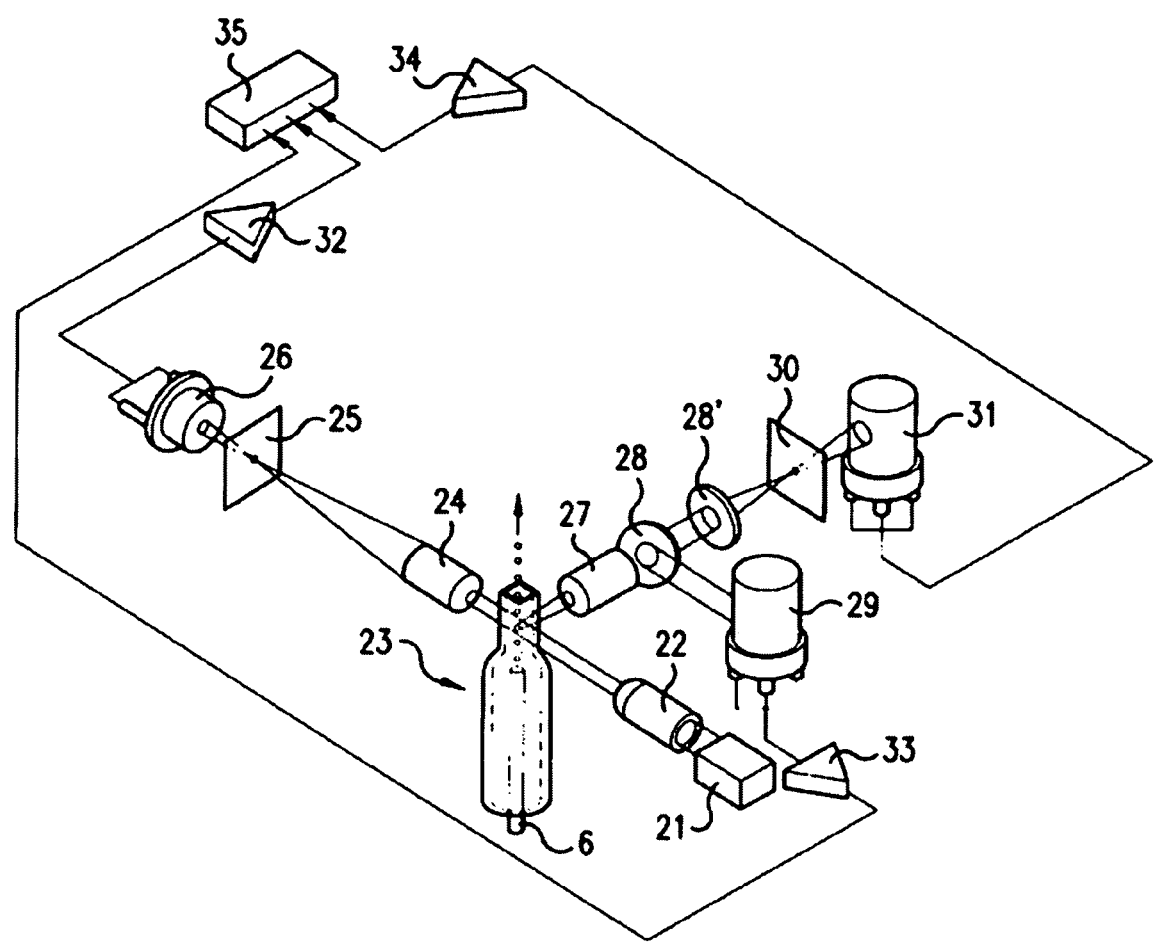
FIG. 4 is a view showing one example of the flow cytometer used in the detection method of this embodiment.
Figure 5:
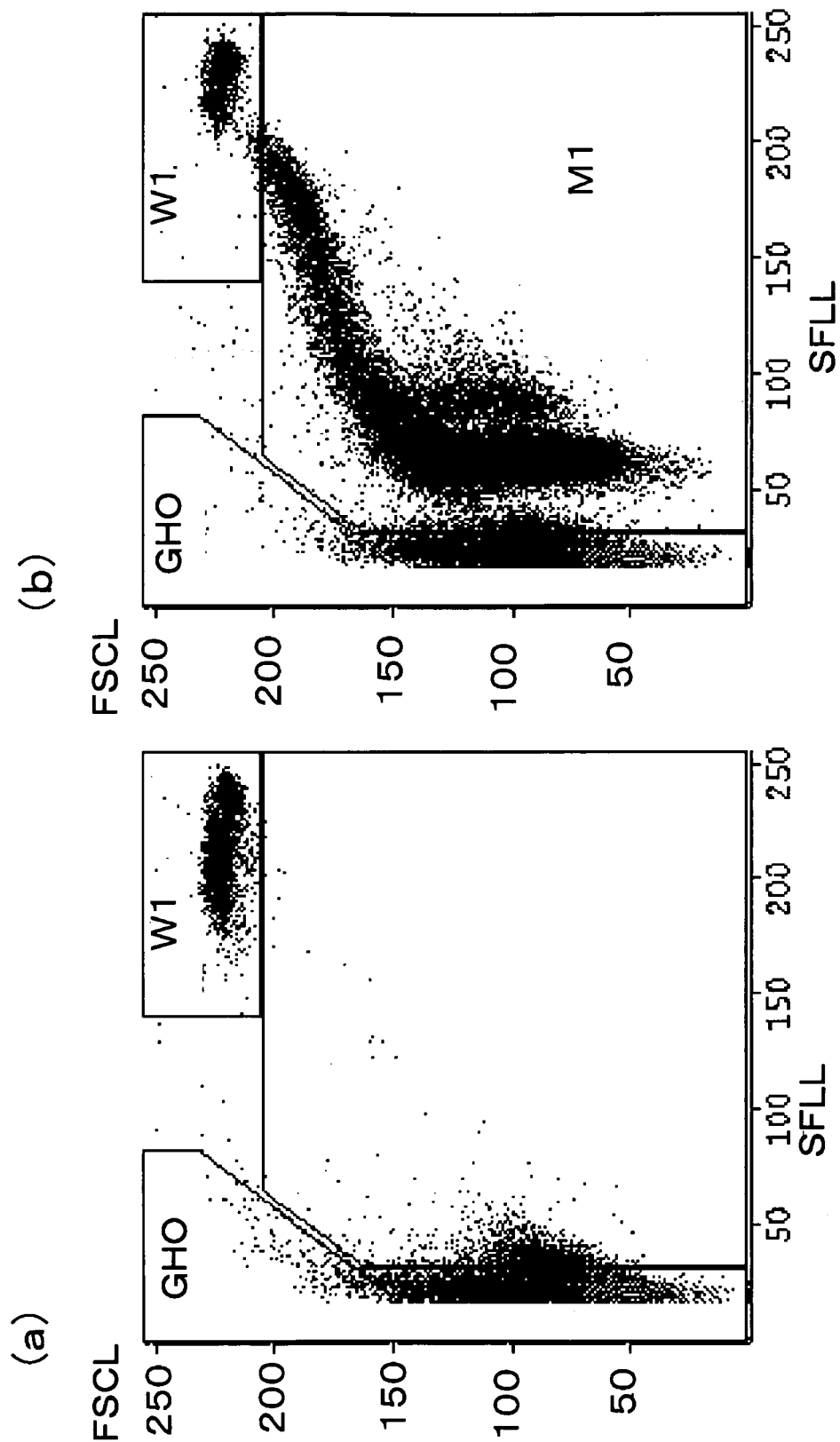
FIGS. 5 (*a*) and (*b*) are scattergrams of measurement samples obtained using Reagent No. 1.
Figure 6:
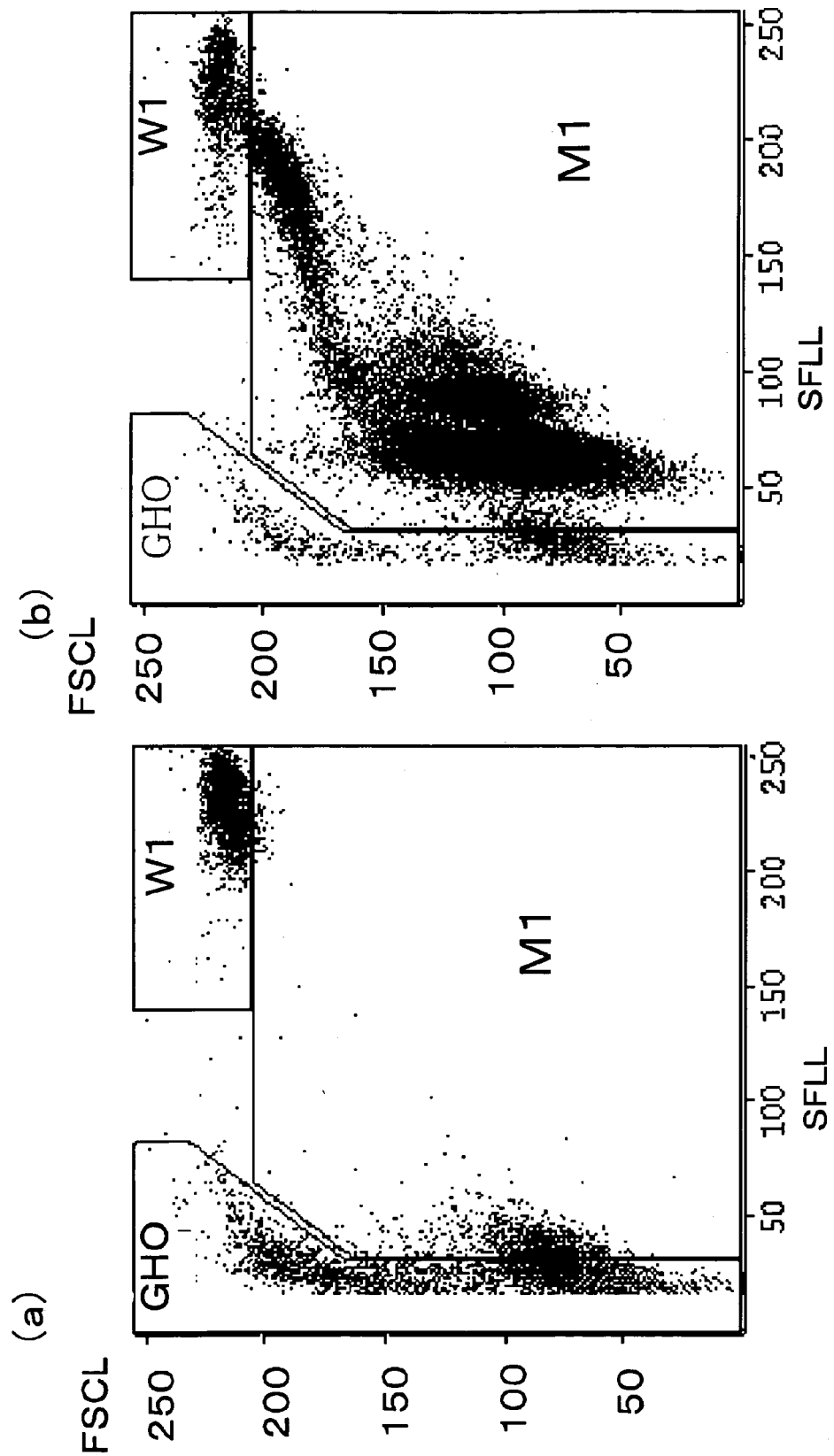
FIGS. 6 (*a*) and (*b*) are scattergrams of measurement samples obtained using Reagent No. 2.
Figure 7:
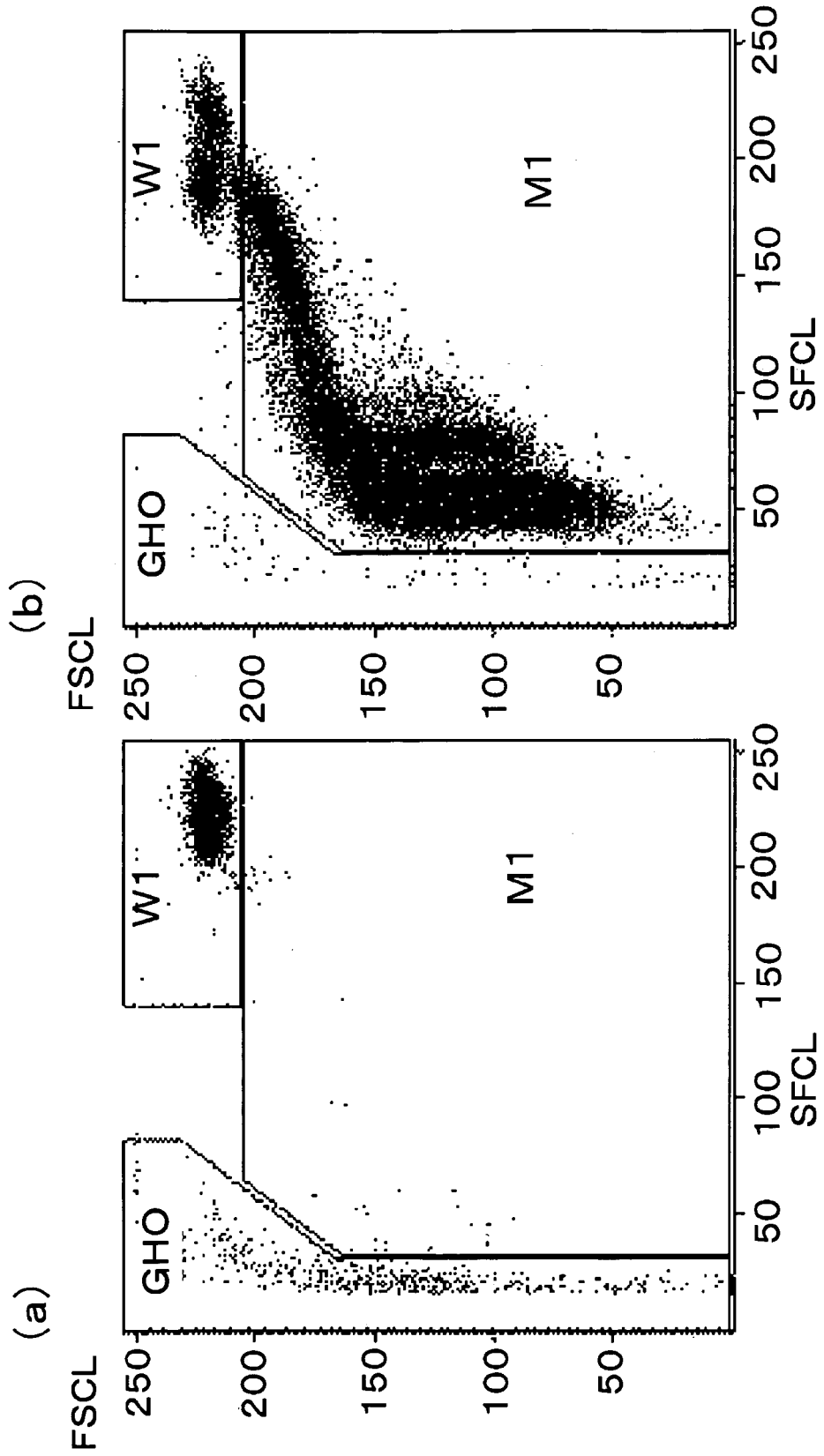
FIGS. 7 (*a*) and (*b*) are scattergrams of measurement samples obtained using Reagent No. 3.
Figure 8:
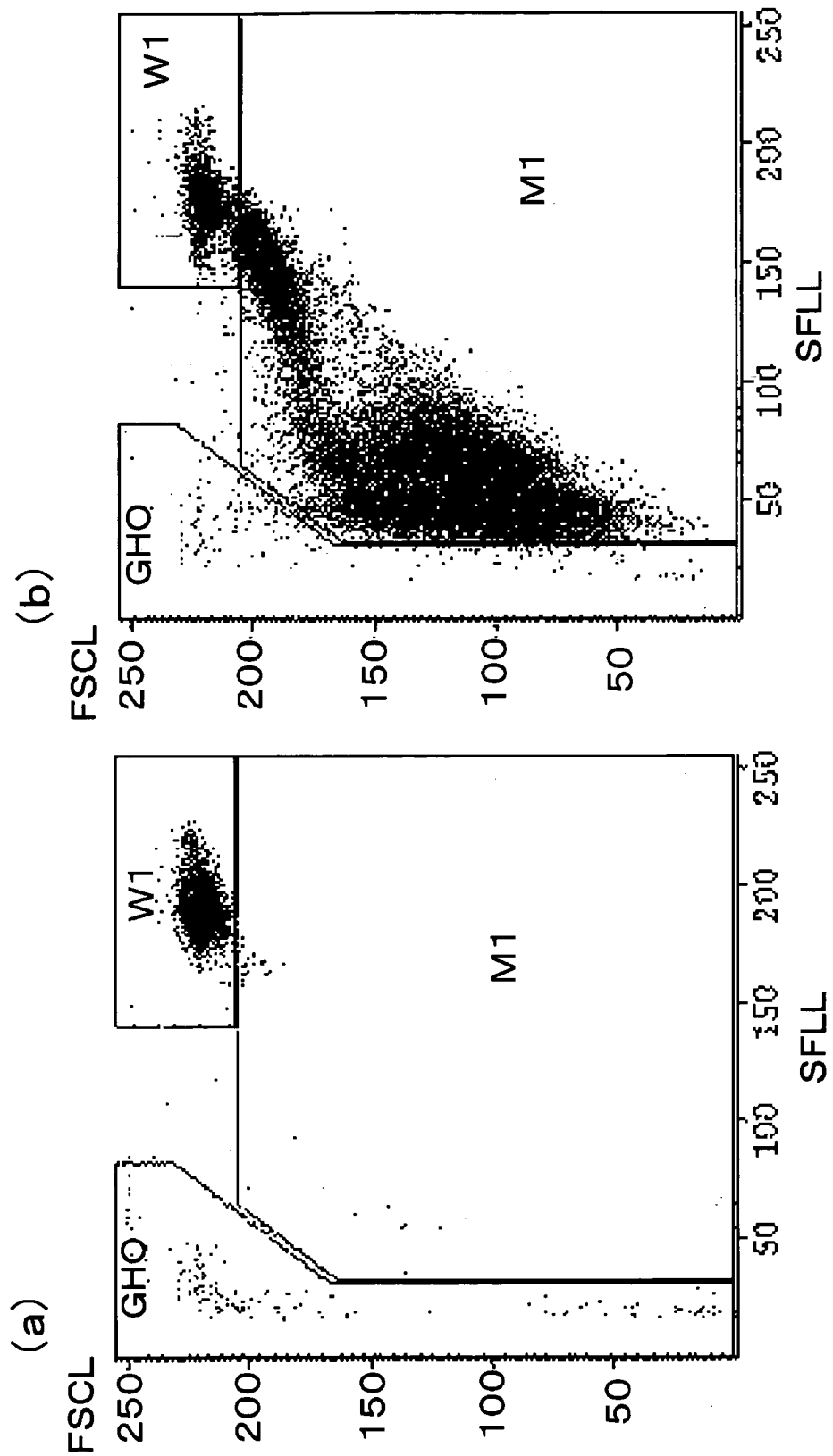
FIGS. 8 (*a*) and (*b*) are scattergrams of measurement samples obtained using Reagent No. 4.
Figure 9:
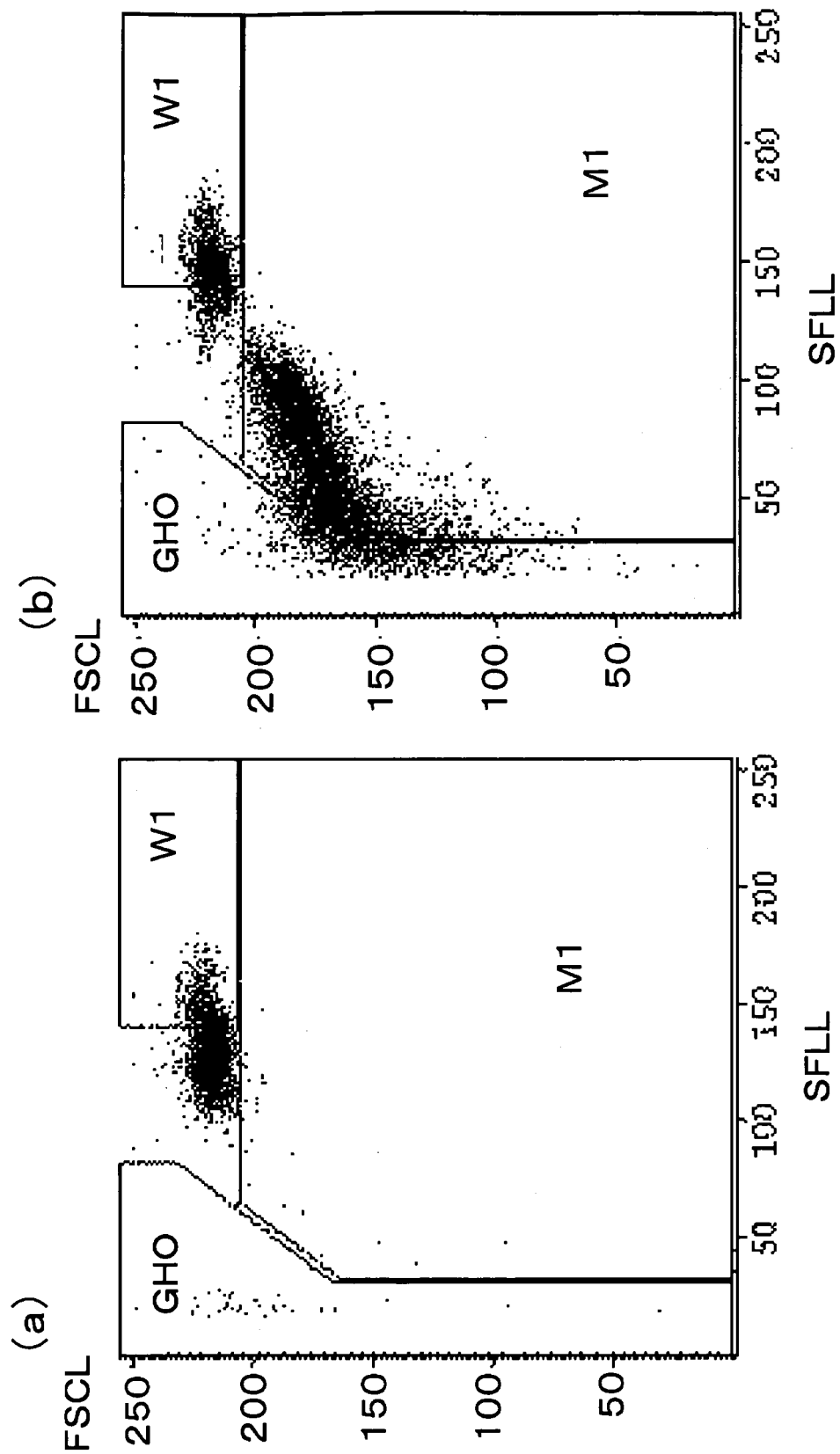
FIGS. 9 (*a*) and (*b*) are scattergrams of measurement samples obtained using Reagent No. 5.

FIG. 4 is one example of the optical system of a flow cytometer used in this embodiment.

In FIG. 4, a beam emitted from an excitation light source (for example, a blue laser diode, wavelength 405 nm) 21 is used to irradiate an orifice of a sheath flow cell 23 via a collimated lens 22. Forward scattered light emitted from blood cells discharged from nozzle 6 and passing through the orifice enters via a light collection lens 24 and a pinhole plate 25 into a forward scattered light detector (photodiode) 26. On the other hand, side scattered light emitted from blood cells passing through the orifice enters via a light collection lens 27 and a dichroic mirror 28 into a side scattered light detector 29 (photomultiplier tube). Side fluorescence emitted from blood cells passing through the orifice enters via the light collection lens 27, the dichroic mirror 28, a filter 29 and a pinhole plate 30 into a side fluorescence detector 31 (photomultiplier tube). The forward scattered light signal emitted from the forward scattered light detector 26, the side scattered light signal emitted from the side scattered light detector 29, and the side fluorescence signal emitted from the side fluorescence detector 31 are amplified by amplifiers 32, 33 and 34 respectively and inputted into an analyzing unit 35.

In the analyzing unit 35, forward scattered light intensity and fluorescence intensity are calculated from the inputted forward scattered light signal and side fluorescence signal respectively, and a 2-dimensional scattergram with the forward scattered light intensity and fluorescence intensity as the parameters is prepared and indicated on an indicator not shown in the figure, and the number of dots (number of particles) in an arbitrary region set in the 2-dimensional scattergram is determined and subjected to arbitrary computation to display counting results and arithmetic results on the indicator.

Further, the flow cytometer is provided preferably with a CCD camera and an image analyzing part. In the detection method in this embodiment, red blood cells maintaining their shape are examined as such by the flow cytometer, and thus an image of infected red blood cells can be displayed and analyzed for the presence of the ring form (multi), the difference between the ring form (single) and ring form (multi) and for distinguishing, on the image, the form of trophozoite-containing red blood cells and schizont-containing red blood cells.

The ring form (single) region and the ring form (multi) region are specified in the embodiments described above, but only one ring form region may be specified.

EXAMPLES

[Detection Reagent]

1. Concentration of Surfactants

Reagents Nos. 1 to 5 were prepared from a reagent for partially lysing a red blood cell membrane having the composition shown in Table 1 by changing the concentrations of the surfactants as shown in Table 2 and adjusting their pH values to 6.1 with hydrochloric acid. 2 μl dye solution containing a dye Hoechst 34580 (excitation wavelength 392 nm and fluorescence wavelength 498 nm, manufactured by Invitrogen Corporation) dissolved in ethylene glycol (0.5 mg/ml), and 1 ml of one of Reagent Nos. 1 to 5, were added to, and mixed at 40° C. for 40 seconds with, 20 μl sample a (human whole blood) or sample b (human whole blood to which cultured malaria parasites were added) to prepare a measurement sample. This measurement sample was measured by a flow cytometer using a blue semiconductor laser (wavelength 405 nm) as a light source.

TABLE 1

| Type | Compound |
| --- | --- |
| Surfactant | LTAC, STAC |
| Buffer agent | Citric acid |
| Osmotic pressure regulating agent | Sodium chloride |
| pH adjusting agent | Hydrochloric acid, sodium hydroxide |
| Diluent | Purified water |

TABLE 2

| Surfactant | Reagent No. | | | | |
| --- | --- | --- | --- | --- | --- |
| (ppm) | 1 | 2 | 3 | 4 | 5 |
| STAC | 90 | — | 90 | 180 | 90 |
| LTAC | — | 900 | 900 | 900 | 2700 |

Scattergrams of samples a and b with Reagent Nos. 1 to 5 are shown in FIGS. 5 to 9, respectively. In each figure, (a) is a scattergram of sample a, and (b) is a scattergram of sample b. In the figure, the GHO gate region is a region of uninfected red blood cells, the W1 gate region is a region of white blood cells, and M1 is a region of infected red blood cells.

As can be seen from FIGS. 5 to 9, the malaria infected red blood cells could be detected with one kind of surfactant at low concentration. For detection of malaria infected red blood cells in a sample of lower infection ratio, however, analysis with only one kind of surfactant is difficult because a part of uninfected red blood cells enters into the region of malaria infected red blood cells, so two or more surfactants should be mixed with each other to balance their respective concentrations. Accordingly, Reagent No. 3 is preferable.

2. Reagent pH

Reagents Nos. 11 to 13 were prepared from a reagent for partially lysing a red blood cell membrane having the composition shown in Table 1 by adding 90 ppm STAC and 900 ppm LTAC as surfactants and regulating the pH value as shown in Table 3 by changing the amount of hydrochloric acid. 2 µl fluorescent dye (Hoechst 34580) used in 1 above, and 1 ml of one of Reagent Nos. 11 to 13, were added to, and mixed at 40° C. for 40 seconds with, 20 µl sample a (human whole blood) or sample b (human whole blood to which cultured malaria parasites were added) to prepare a measurement sample. This measurement sample was measured by a flow cytometer using a blue semiconductor laser as a light source.

TABLE 3

| Reagent No. | pH |
|---|---|
| 11 | 3.0 |
| 12 | 6.0 |
| 13 | 8.0 |

Figure 10:
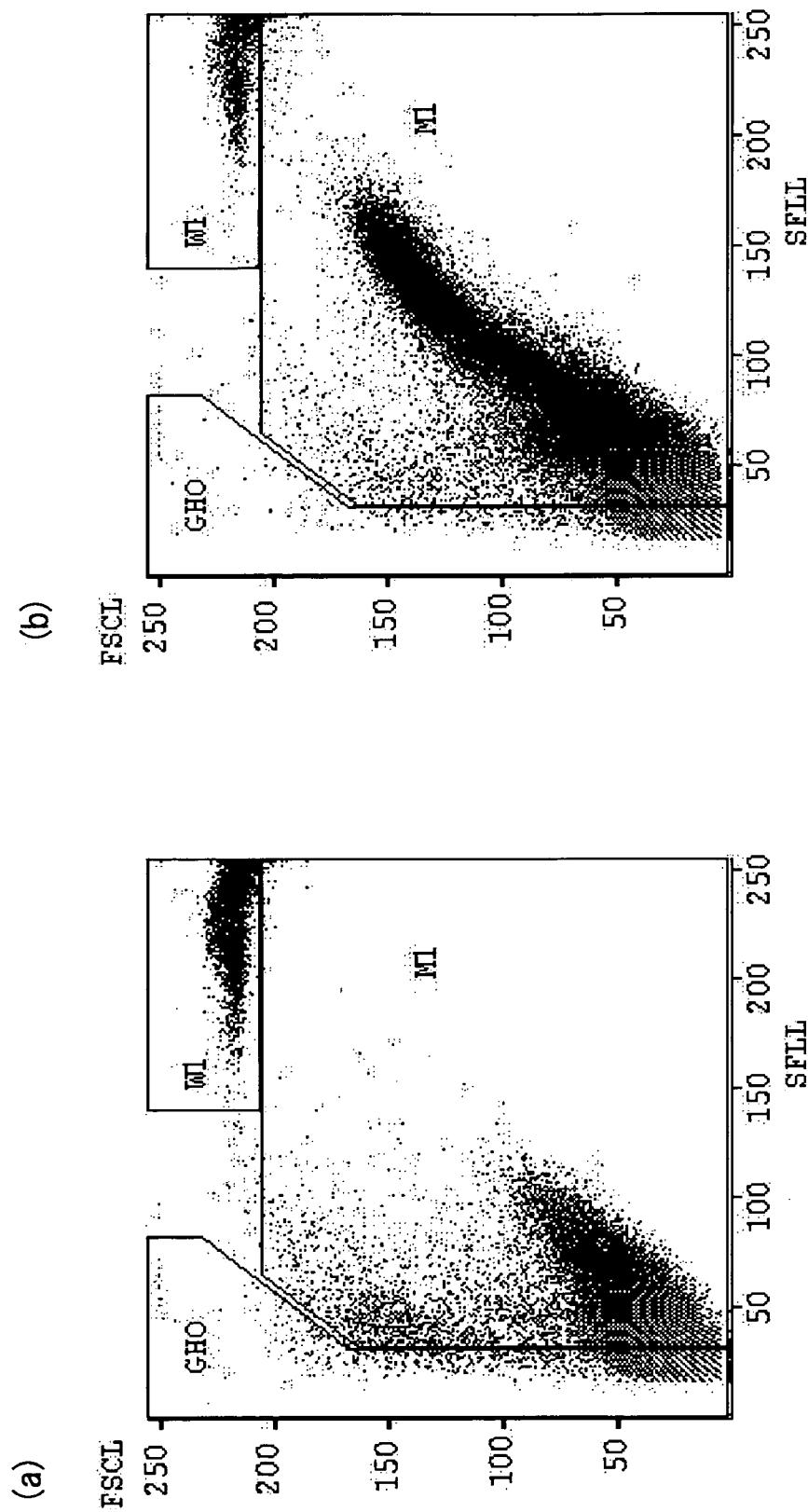
FIGS. 10 (*a*) and (*b*) are scattergrams of measurement samples obtained using Reagent No. 11.
Figure 11:
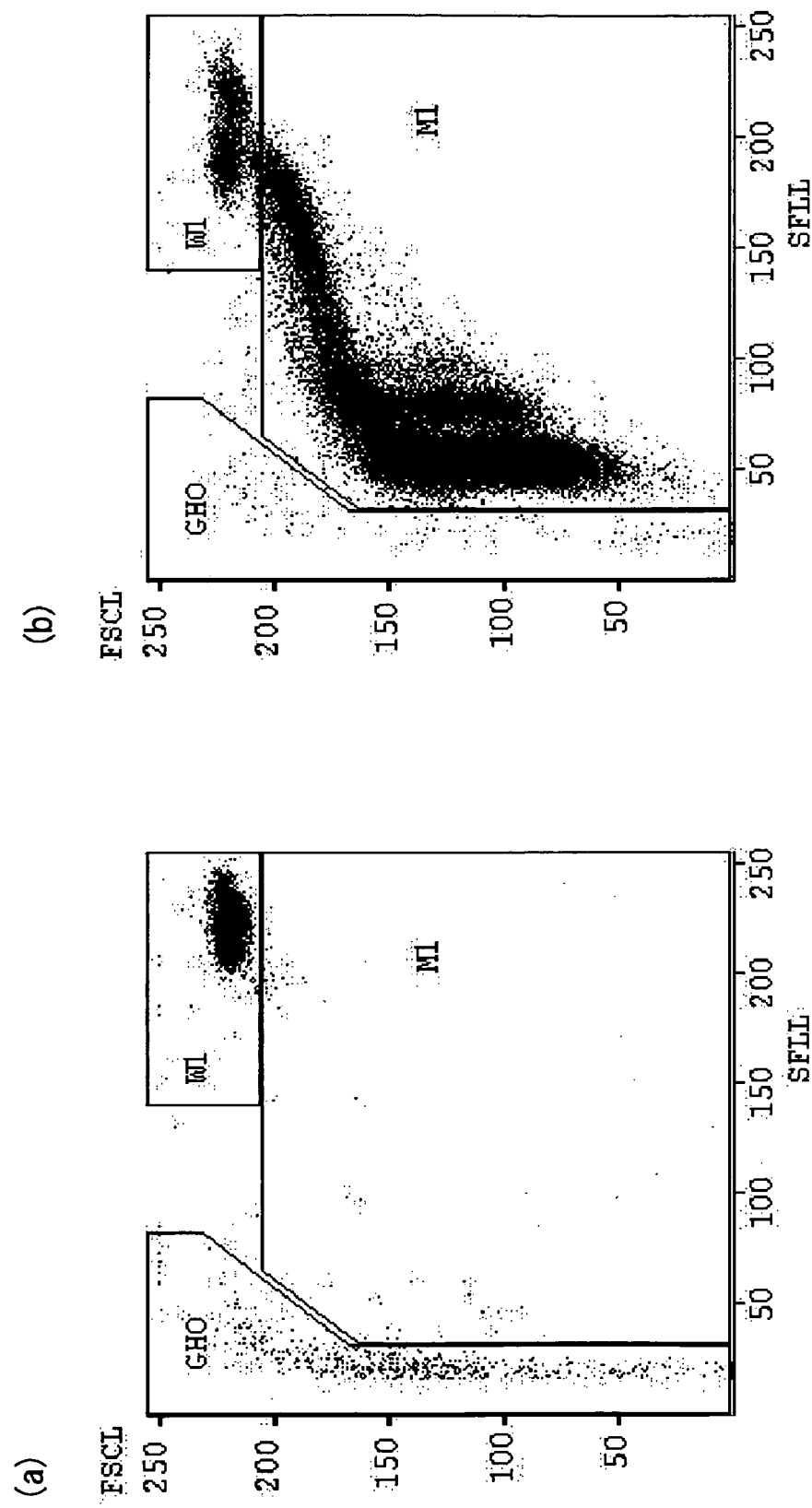
FIGS. 11 (*a*) and (*b*) are scattergrams of measurement samples obtained using Reagent No. 12.
Figure 12:
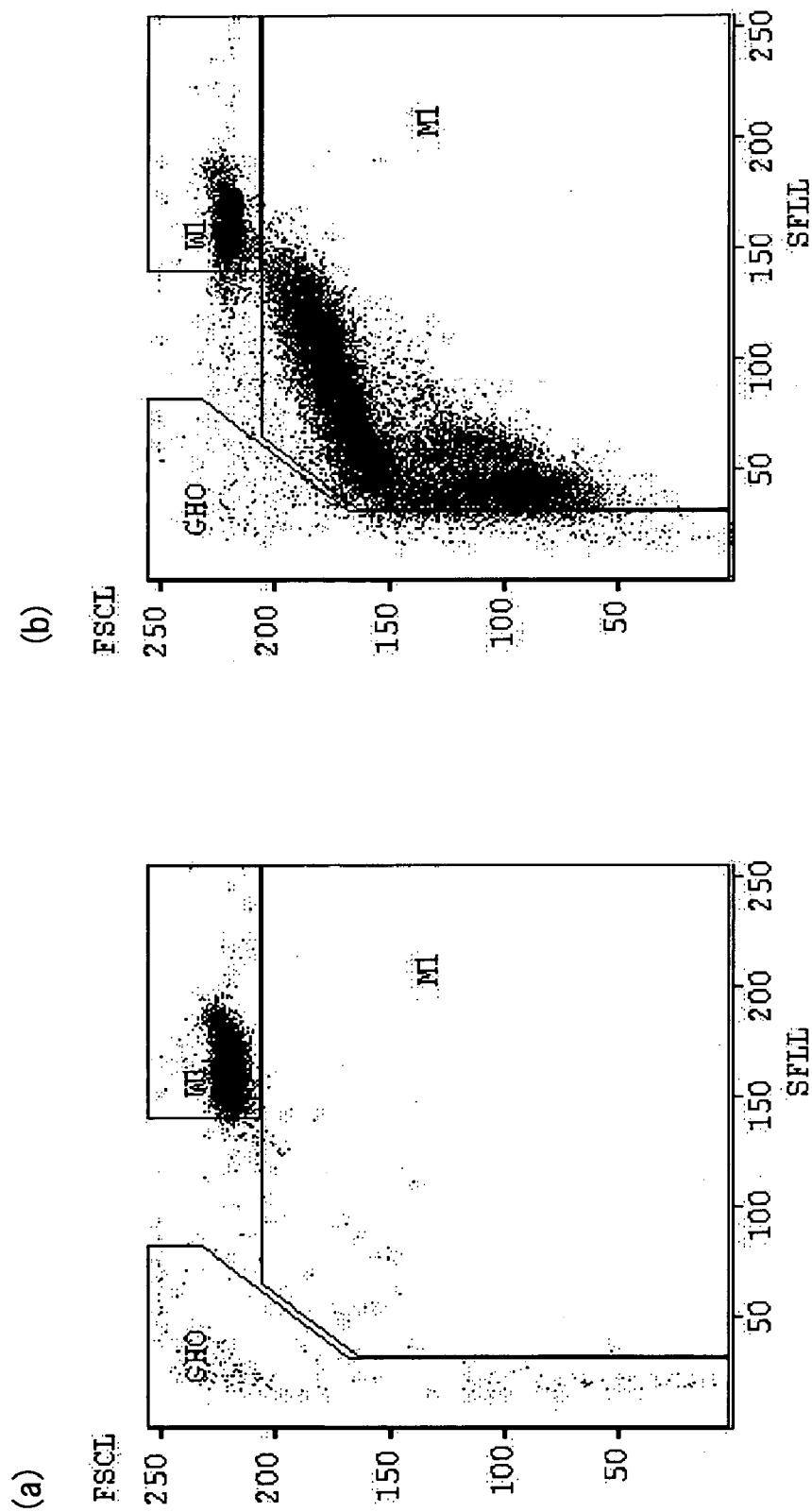
FIGS. 12 (*a*) and (*b*) are scattergrams of measurement samples obtained using Reagent No. 13.

Scattergrams of samples a and b with Reagent Nos. 11 to 13 are shown in FIGS. 10 to 12. In each figure, (a) is a scattergram of sample a, and (b) is a scattergram of sample b. In the figure, the GHO gate region is a region of uninfected red blood cells, the W1 gate region is a region of white blood cells, and M1 is a region of infected red blood cells.

As can be seen from comparison among FIGS. 10 to 12, the reagent should be Reagent No. 12 in order that the sample b is distinguished from the GHO region and appears in the M1 region.

3. Osmotic Pressure of the Reagent

The osmotic pressure was measured by Advanced 3D3 Osmometer (cryoscopic method) manufactured by Advanced Instruments, INC.

Reagents Nos. 21 to 23 were prepared from a reagent for partially lysing a red blood cell membrane having the composition shown in Table 1 (90 ppm STAC and 900 ppm LTAC as surfactants, pH 6.1) by changing the osmotic pressure as shown in Table 4 by mixing a different amount of sodium chloride. 2 µl dye solution containing Hoechst 34580 used above, and 1 ml of one of Reagent Nos. 21 to 23, were added to, and mixed at 40° C. for 40 seconds with, 20 µl sample a (human whole blood) or sample b (human whole blood to which cultured malaria parasites were added) to prepare a measurement sample. This measurement sample was measured by a flow cytometer using a blue semiconductor laser as a light source.

TABLE 4

| Reagent No. | Osmotic pressure (mOsm/kg · $H_2O$) |
|---|---|
| 21 | 100 |
| 22 | 250 |
| 23 | 350 |

Figure 13:
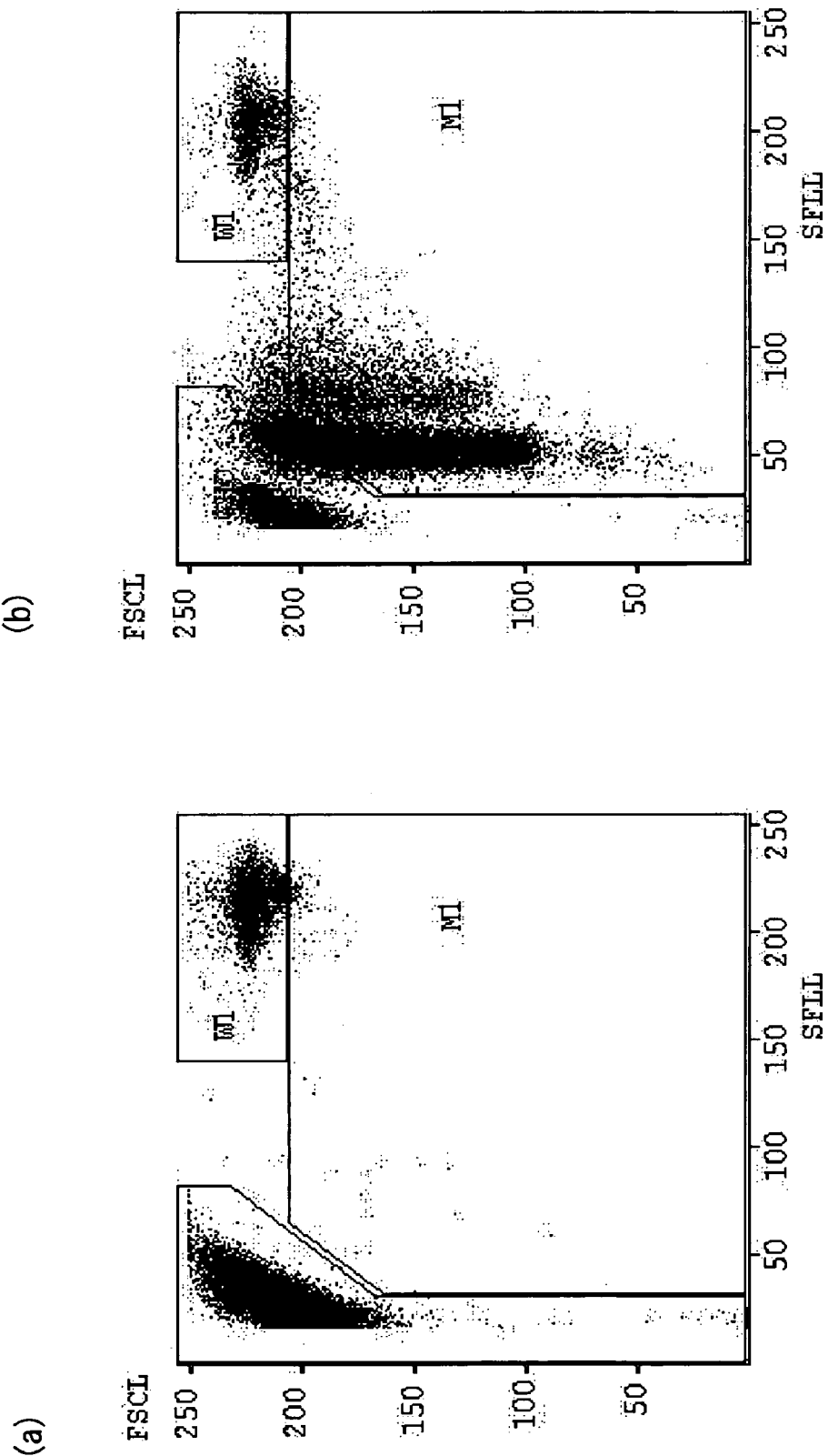
FIGS. 13 (*a*) and (*b*) are scattergrams of measurement samples obtained using Reagent No. 21.
Figure 14:
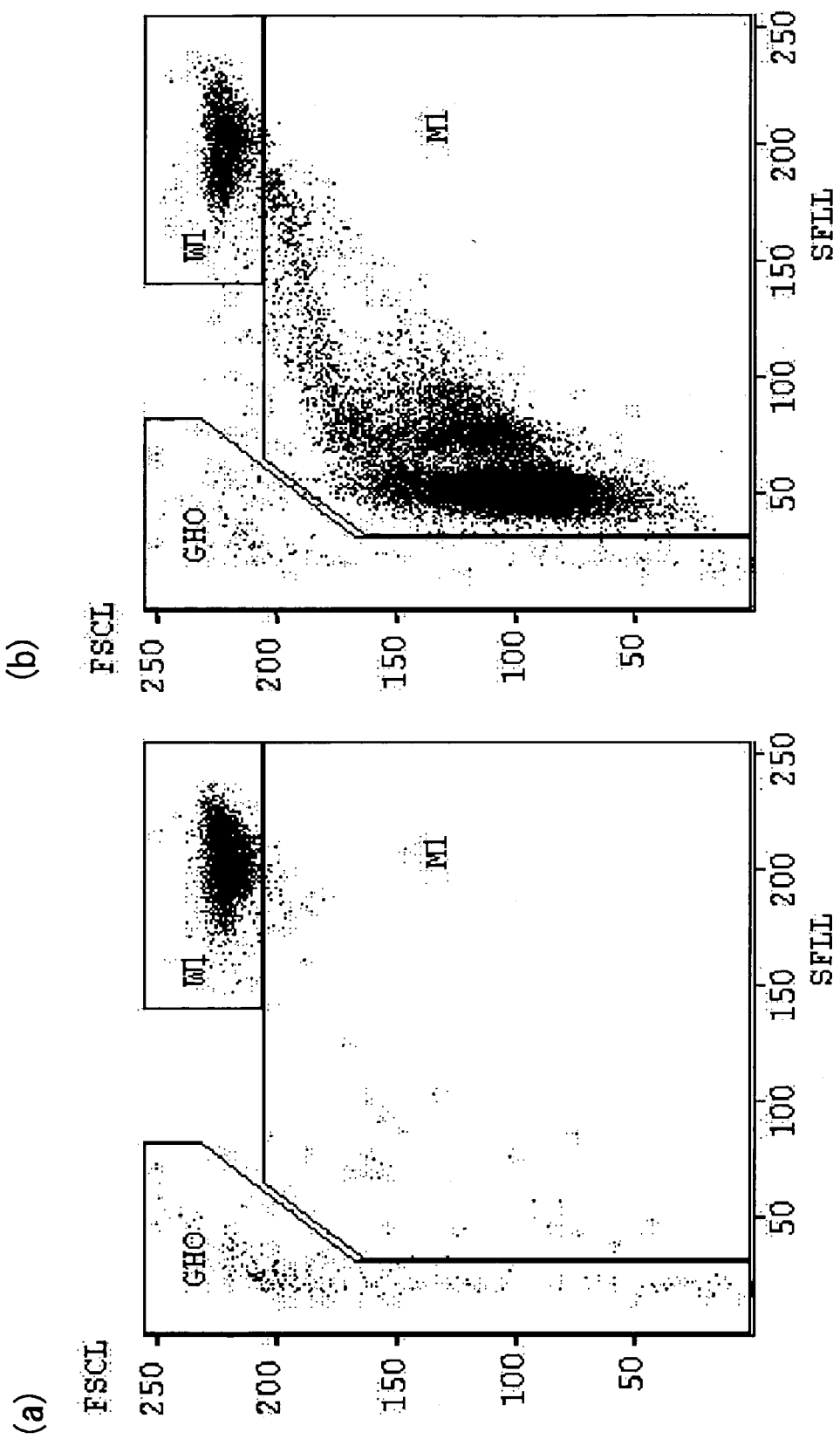
FIGS. 14 (*a*) and (*b*) are scattergrams of measurement samples obtained using Reagent No. 22.
Figure 15:
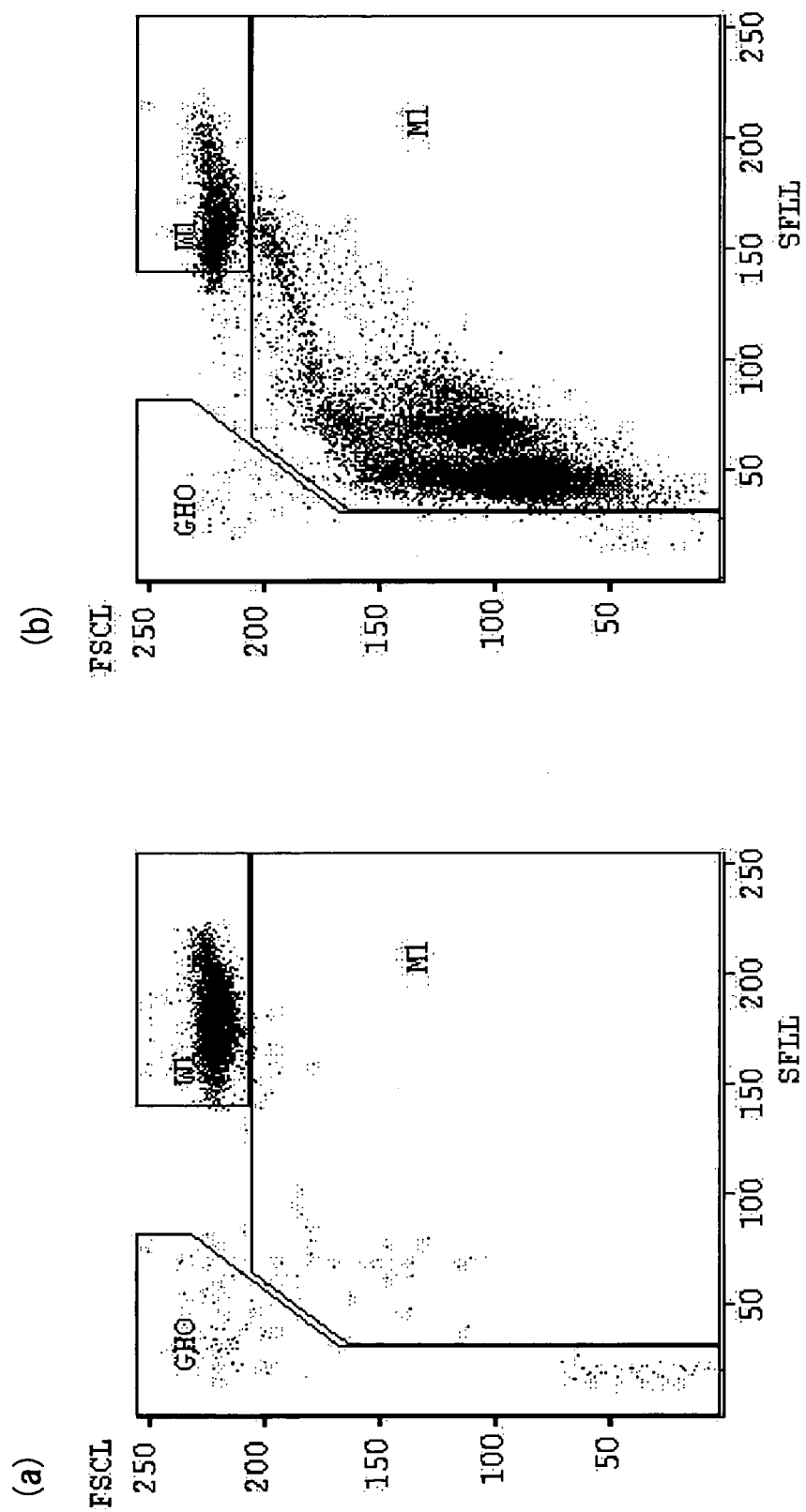
FIGS. 15 (*a*) and (*b*) are scattergrams of measurement samples obtained using Reagent No. 23.

Scattergrams of samples a and b with Reagent Nos. 21 to 23 are shown in FIGS. 13 to 15. In each figure, (a) is a scattergram of sample a, and (b) is a scattergram of sample b. In the figure, the GHO gate region is a region of uninfected red blood cells, the W1 gate region is a region of white blood cells, and M1 is a region of infected red blood cells.

As can be seen from comparison among FIGS. 13 to 15, the reagent should be Reagent No. 22 in order that the sample b is distinguished from the GHO region and appears in the M1 region.

[Detection of Red Blood Cells Multi-infected with Malaria]

Example 1

1 ml reagent for partially lysing a red blood cell membrane, which had the composition shown in Table 1 (90 ppm STAC and 900 ppm LTAC as surfactants, pH 6.1, osmotic pressure 256 mOsm/kg·$H_2O$), was mixed with 2 µl Hoechst 34580 dye solution used above, to prepare a detection reagent.

The above detection reagent was mixed with a sample having 20 µl cultured malaria mixed at 40° C. for 40 seconds with human whole blood, to prepare a measurement sample.

Figure 16:
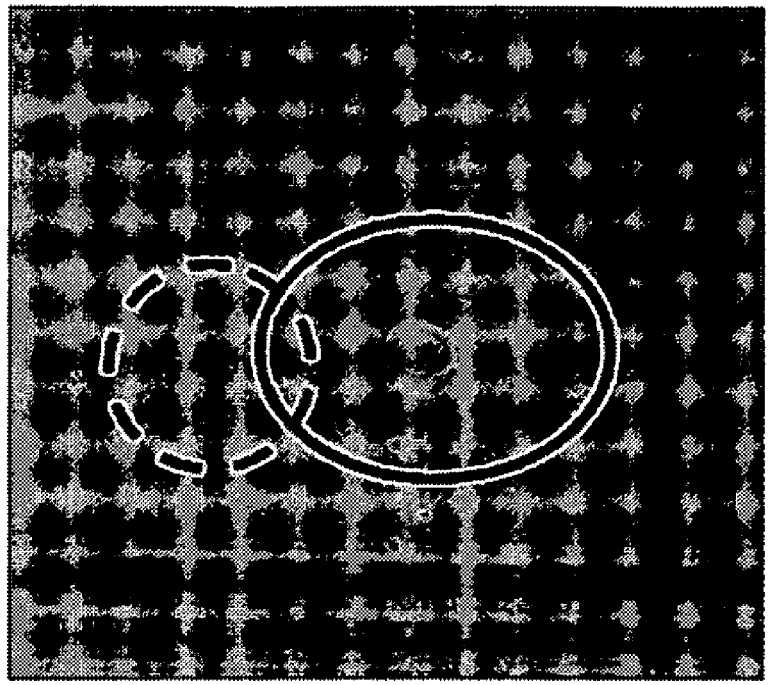
FIG. 16 is (a) a phase contrast microphotograph (×1000) and (b) a fluorescence microphotograph (×1000) of a ring form (single) present in the sample in Example 1.
Figure 16:
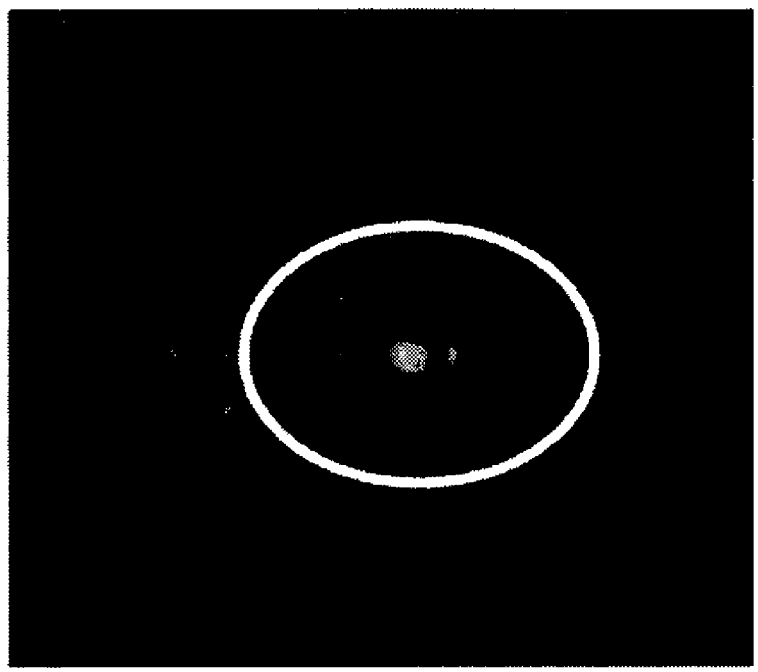
Figure 17:
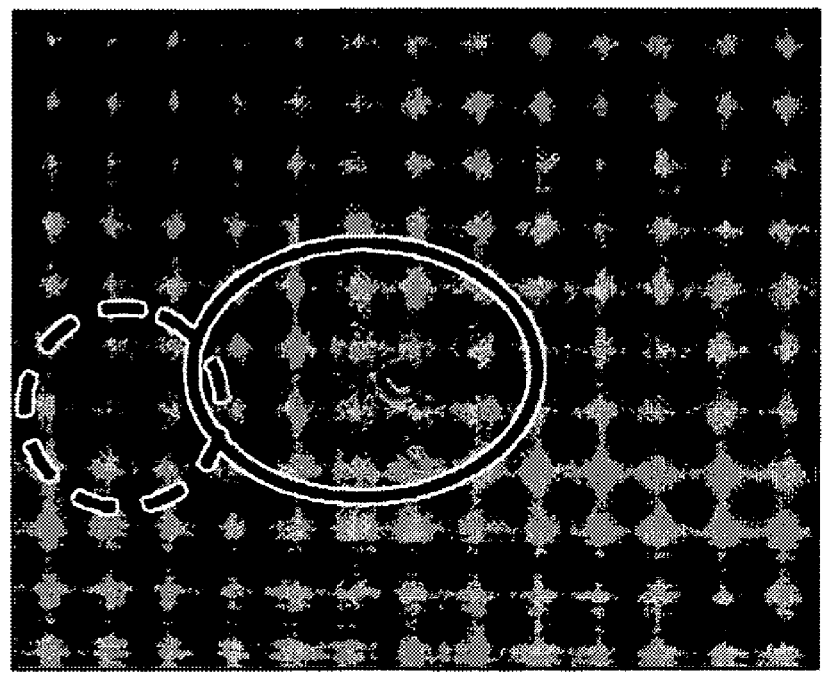
FIG. 17 is (a) a phase contrast microphotograph (×1000) and (b) a fluorescence microphotograph (×1000) of a ring form (double) present in the sample in Example 1.
Figure 17:
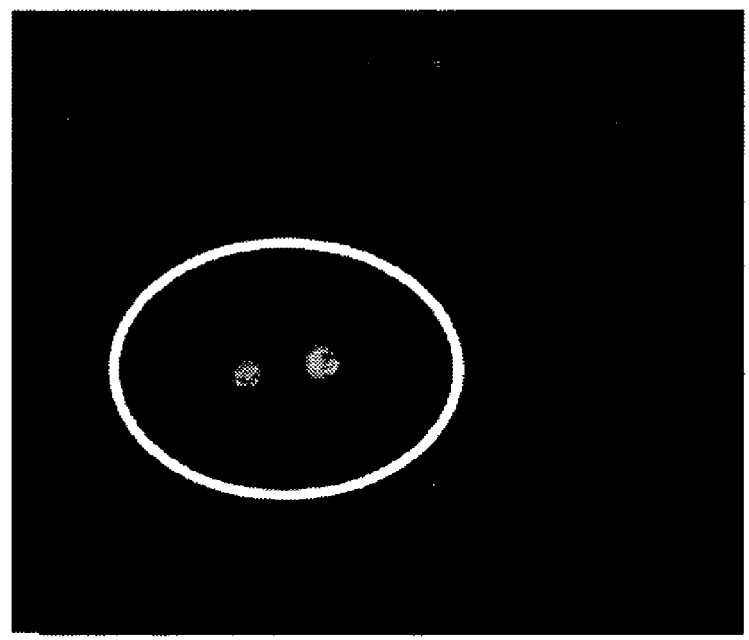

When this measurement sample was observed under a phase contrast microscope and a fluorescence microscope, a ring form (single) and a ring form (multi) maintaining the form of red blood cell were recognized. The respective microphotographs are shown in FIGS. 16 and 17 respectively.

Figure 18:
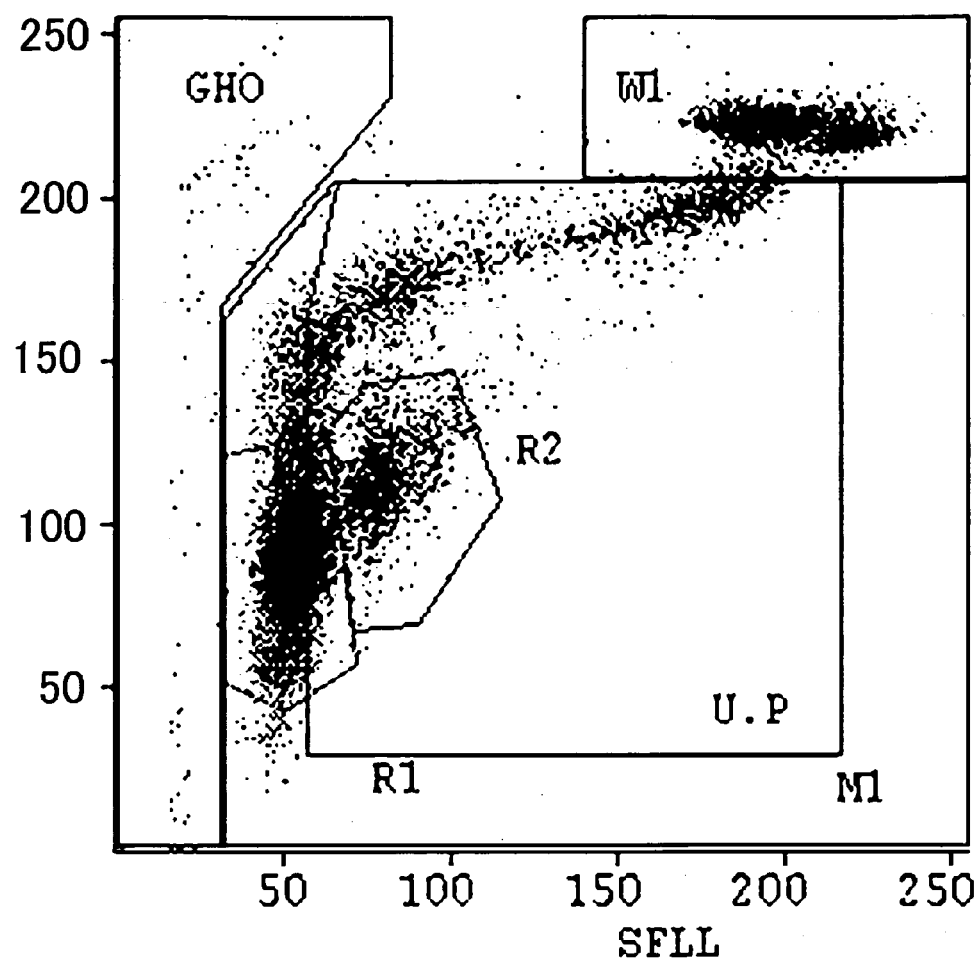
FIG. 18 is a scattergram obtained in Example 1.

Then, this measurement sample was measured by a flow cytometer using a blue semiconductor laser as a light source to prepare a scattergram with fluorescence intensity on the abscissa and scattered light intensity on the ordinate, and each region was specified as shown in FIG. 18. Dots in the R1 gate region (ring form (single)) and in the R2 gate region (ring form (multi)) were counted to determine the ratio (R2/(R1+R2)) of the ring form (multi) in the ring form-containing red blood cells.

A smear of the same malaria infected sample was prepared, subjected to Giemsa staining and observed under a microscope. The ring form (single) and ring form (multi) were counted twice respectively to calculate the mean, to determine the ratio (R2/(R1+R2)) of the ring form (multi) in the ring form-containing red blood cells.

The counting results based on the scattergram and the counting results based on observation under a microscope are shown respectively in Table 5.

TABLE 5

| | Flow cytometer | Visual check | | |
|---|---|---|---|---|
| | | first time | second time | mean |
| Ring form (single) | 6690 | 63 | 59 | 61 |
| Ring form (multi) | 1532 | 14 | 15 | 14.5 |
| Ratio (%) of ring form (multi) in the ring form-containing red blood cells | 18.6 | 19.2 | 20.3 | 19.2 |

As can be seen from Table 5, the ratio of the ring form (multi) in the ring form-containing red blood cells was 18.6% in the method in this example and 19.2% in the conventional method of observation under a microscope. It could be confirmed that by specifying and counting dots in the region in the measurement method in this example using a flow cytometer, the ratio of the ring form (multi) can be determined with the same accuracy as by counting cells while confirming the shape by observation under a microscope.

Example 2

1 ml reagent for partially lysing a red blood cell membrane, which had the composition shown in Table 6 (281 ppm STAC and 924 ppm LTAC as surfactants, pH 6.1, osmotic pressure 257 mOsm/kg·$H_2O$), was mixed with 2 µl Hoechst 34580 dye solution used above, to prepare a detection reagent.

TABLE 6

| Type | Compound |
| --- | --- |
| Surfactant | LTAC, STAC |
| Buffer agent | Citric acid |
| Osmotic pressure regulating agent | Sodium chloride |
| pH adjusting agent | Hydrochloric acid, sodium hydroxide |
| Diluent | Purified water |

As the measurement sample, a tertian malaria infected sample was used.

Figure 19:
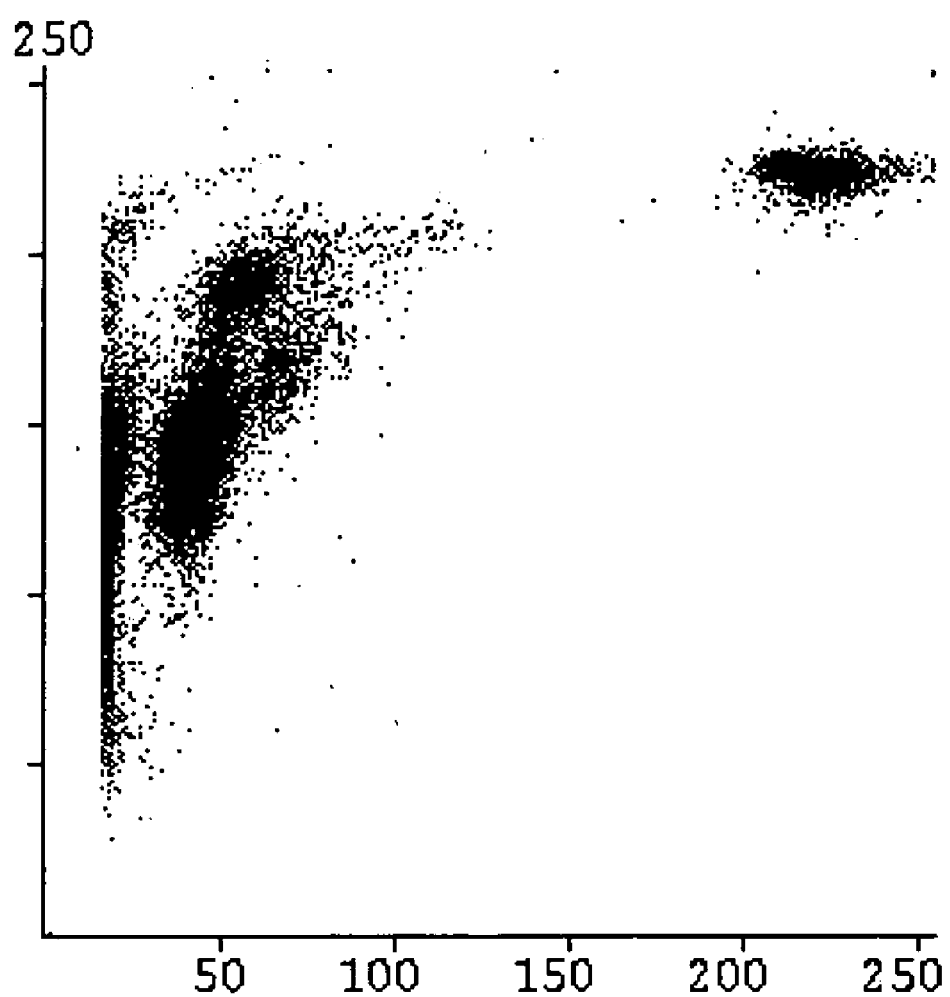
FIG. 19 is a scattergram obtained in Example 2.

Then, this measurement sample was mixed with the above detection reagent and measured by a flow cytometer using a blue semiconductor laser as a light source to prepare a scattergram with fluorescence intensity on the abscissa and scattered light intensity on the ordinate as shown in FIG. 19. On the basis of this scattergram, the malaria particle count and malaria infection ratio were determined by Method A described above. The correction constant K used in calculation of infection ratio by Method A is 1. The results together with those by visual check are shown in Table 7.

TABLE 7

| | Malaria particle count | Infection ratio |
| --- | --- | --- |
| Visual check | — | 0.28% |
| Example 2 | 8616 | 0.31% |
| Example 3 | 8312 | 0.29% |
| Example 4 | 8556 | 0.28% |

As can be seen from Table 7, the malaria infection ratio was 0.31% in the method in Example 2 and 0.28% in the conventional method (visual check) of observation under a microscope. It could thus be confirmed that when the method in Example 2 is used, the infection ratio can be determined with the same accuracy as by counting cells while confirming the shape by observation under a microscope.

Example 3

1 ml reagent for partially lysing a red blood cell membrane, which had the composition shown in Table 8 (281 ppm STAC, 924 ppm LTAC and 500 ppm polyoxyethylene (20) phytosterol as surfactants, pH6.1, osmotic pressure 257 mOsm/kg·H$_2$O), was mixed with 2 µl Hoechst 34580 dye solution used above, to prepare a detection reagent.

TABLE 8

| Type | Compound |
| --- | --- |
| Surfactant | LTAC, STAC, Polyoxyethylene(20) Phytosterol |
| Buffer agent | Citric acid |
| Osmotic pressure regulating agent | Sodium chloride |
| pH adjusting agent | Hydrochloric acid, sodium hydroxide |
| Diluent | Purified water |

As the measurement sample, the same tertian malaria infected sample as in Example 2 was used.

Figure 20:
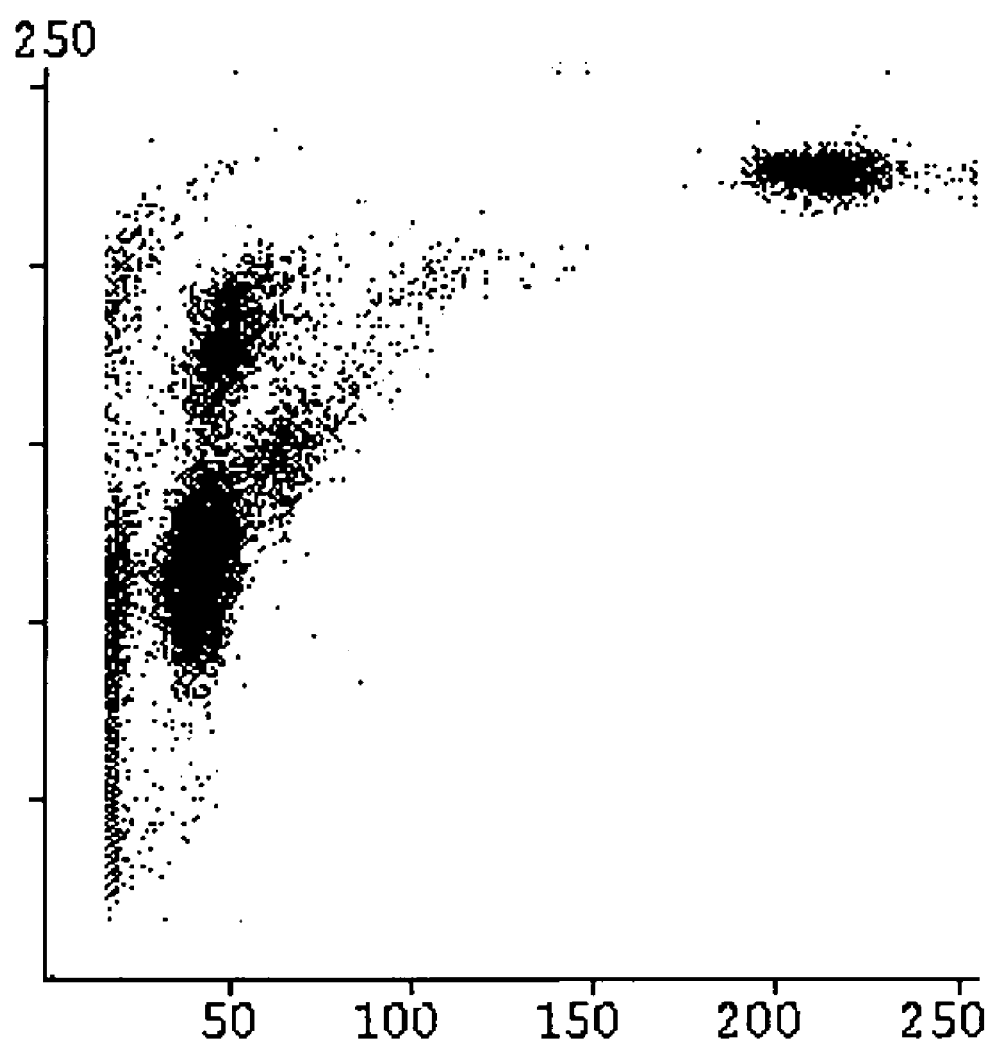
FIG. 20 is a scattergram obtained in Example 3.

Then, this measurement sample was mixed with the above detection reagent and measured by a flow cytometer using a blue semiconductor laser as a light source, to prepare a scattergram with fluorescence intensity on the abscissa and scattered light intensity on the ordinate as shown in FIG. 20. On the basis of this scattergram, the malaria particle count and malaria infection ratio were determined by the same method as in Example 2. The results together with those by visual check are shown in Table 7.

As can be seen from Table 7, the malaria infection ratio was 0.29% in the method in Example 3 and 0.28% in the conventional method (visual check) of observation under a microscope. It could thus be confirmed that when the method in Example 3 is used, the infection ratio can be determined with the same accuracy as by counting cells while confirming the shape by observation under a microscope.

It may also be confirmed that the groups of the each growth stage are distinguished more clearly on the scattergram in FIG. 20 than by the method in Example 2 not using a nonionic surfactant in the reagent for partially lysing a red blood cell membrane.

Example 4

1 ml reagent for partially lysing a red blood cell membrane, which had the composition shown in Table 9 (281 ppm STAC, 924 ppm LTAC and 500 ppm polyoxyethylene (25) phytostanol as surfactants, pH6.1, osmotic pressure 257 mOsm/kg·H$_2$O), was mixed with 2 µl Hoechst 34580 dye solution used above, to prepare a detection reagent.

TABLE 9

| Type | Compound |
| --- | --- |
| Surfactant | LTAC, STAC, Polyoxyethylene(25) Phytostanol |
| Buffer agent | Citric acid |
| Osmotic pressure regulating agent | Sodium chloride |
| pH adjusting agent | Hydrochloric acid, sodium hydroxide |
| Diluent | Purified water |

As the measurement sample, the same tertian malaria infected sample as in Examples 2 and 3 was used.

Figure 21:
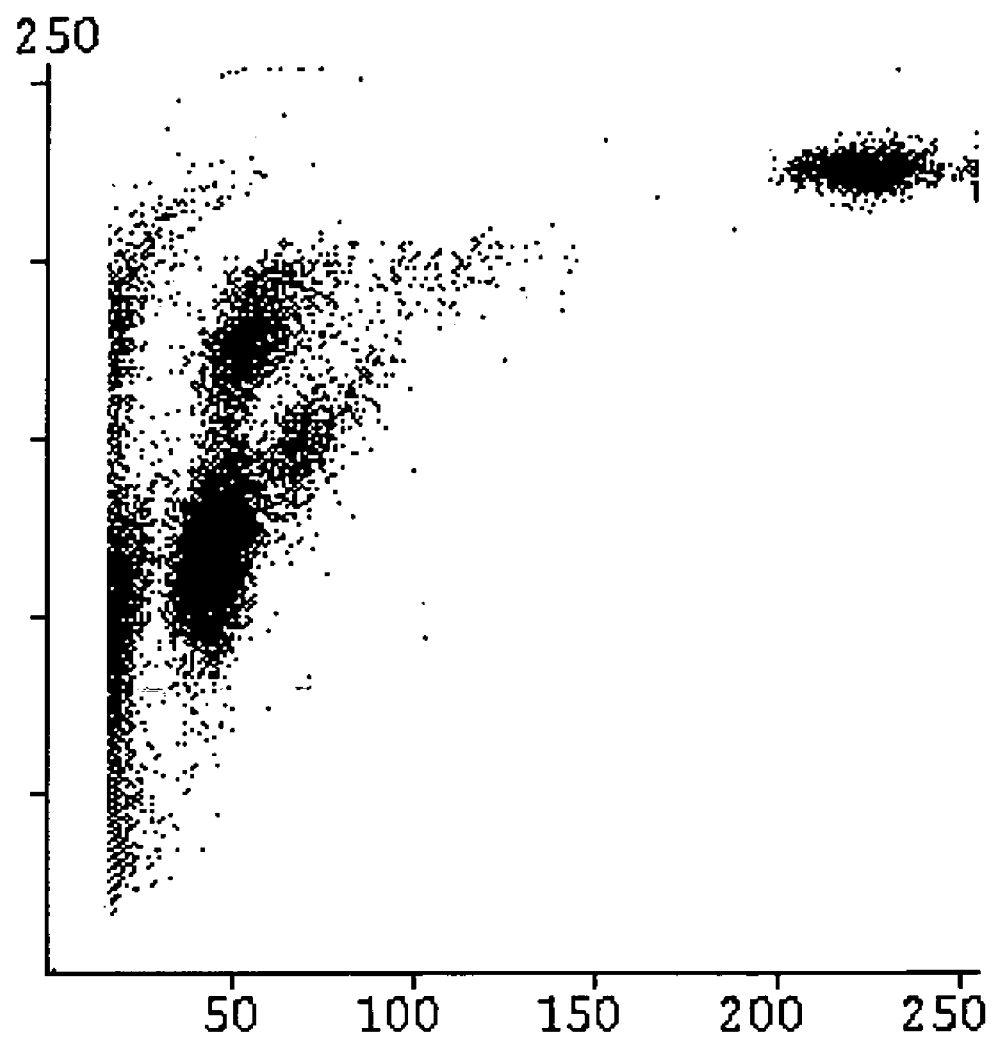
FIG. 21 is a scattergram obtained in Example 4.

Then, this measurement sample was mixed with the above detection reagent and measured by a flow cytometer using a blue semiconductor laser as a light source, to prepare a scattergram with fluorescence intensity on the abscissa and scattered light intensity on the ordinate as shown in FIG. 21. On the basis of this scattergram, the malaria particle count and malaria infection ratio were determined by the same method as in Examples 2 and 3. The results together with those by visual check are shown in Table 7.

As can be seen from Table 7, the malaria infection ratio was 0.28% in the method in Example 4 and 0.28% in the conventional method (visual check) of observation under a microscope. It could thus be confirmed that when the method in Example 4 is used, the infection ratio can be determined with the same accuracy as by counting cells while confirming the shape by observation under a microscope.

It may also be confirmed that the groups of the each growth stage are distinguished more clearly on the scattergram in FIG. 21 than by the method in Example 2 not using a nonionic surfactant in the reagent for partially lysing a red blood cell membrane.

The reagent for partially lysing a red blood cell membrane in this embodiment can be used to prepare a measurement sample with red blood cells maintaining their form, applicable as such to a flow cytometer, and can thus be applied where it is desired to observe not only the distribution of cells based on fluorescence intensity but also the form of red blood cells.

The detection method in this embodiment can be used to know the infection ratio and the ratio of red blood cells containing malaria parasites in a predetermined growth stage, rapidly and easily with accuracy comparable with that by counting cells while actually observing the shape under a microscope. Accordingly, problems such as poor reproducibility of results and difference in detection limit, depending on the skills of a technician who observes a sample under a microscope, can be avoided. Further, the detection method of the embodiment can prevent subjective judgment made by the technician thereby providing more objective examination results. In the actual medical field, the detection method of the embodiment can be used in rapid diagnosis and in selection of a therapeutic method.including the determination of the dose of a medicine administered, the administration span etc.

The detection method of the embodiment can also be utilized in fields of research such as elucidation of the mechanism of infection with malaria parasites and creation of anti-malaria drugs and in other studies requiring confirmation of the infection ratio and growth state of malaria parasites. For example, it is possible to select more effective medicine by classifying malaria infected red blood cells into each growth stage accurately by the method of this embodiment when the medicine for curing malaria is developed. Specifically, while malaria infected red blood cells of each growth stage are detected when the red blood cells have been infected by cultivated malaria parasites, only malaria infected red blood cells containing ringforms may be detected when predetermined medicine for curing malaria is added. This means that the medicine for curing malaria prevents ringforms from growing to trophozoites. On the other hand, if malaria infected red blood cells of each growth stage are detected at comparable level even if the medicine for curing malaria is added, this means that the medicine is not so effective for preventing malaria parasites from rowing.

As described above, the reagent for partially lysing a red blood cell membrane in this embodiment permits a fluorescent dye to penetrate into a red blood cell and simultaneously allows malaria parasites to be retained in the red blood cell, and thus the reagent for detecting infected red blood cells, which comprises the reagent for partially lysing a red blood cell membrane and a DNA-selective bisbenzimide type fluorescent dye, can distinguish and detect malaria infected red blood cells, such as ring form (multi) and ring form (single), which are different in the total amount of DNA.

The method of detecting malaria parasites in this embodiment uses, in a flow cytometer, the reagent capable of permitting a fluorescent dye to penetrate into a red blood cell and simultaneously allowing malaria parasites to be retained in the red blood cell, and thus the method can distinguish and detect malaria parasites while distinguishing the ring form (multi) from the ring form (single). By using the detection result, tropical malaria and other malaria can be distinguished from each other.

In the method of detecting malaria infected red blood cells in this embodiment, malaria infected red blood cells different in the total amount of DNA can be distinguished, and the ring form (multi) can be detected as one infected red blood cell, and thus the infection ratio can be determined with accuracy equal to or higher than the infection ratio determined by the conventional method of observation under a microscope.

What is claimed is:

1. A reagent for partially lysing a cell membrane of a red blood cell infected with a malaria parasite, comprising:
   a fluorescent dye;
   a first surfactant which has predetermined lysing ability for the red blood cell membrane;
   a second surfactant which has weaker lysing ability than that of the first surfactant; and
   an osmotic pressure regulating agent for regulating an osmotic pressure of the reagent,
   wherein the reagent has the osmotic pressure of 200 to 300 mOsm/kg·$H_2$; and
   wherein the reagent partially lyses the malaria infected red blood cell membrane such that a malaria parasite is retained in the red blood cell and fluorescent dye passes through the cell membrane.

2. The reagent of claim 1,
   wherein the first and second surfactant are quaternary ammonium salts which have long chain alkyl groups; and
   wherein a carbon number of the alkyl group of the second surfactant is smaller than that of the alkyl group of the first surfactant.

3. The reagent of claim 1,
   wherein the first surfactant is stearyl trimethyl ammonium chloride, and the second surfactant is lauryl trimethyl ammonium chloride.

4. The reagent of claim 1, further comprising:
   a nonionic surfactant which substantially does not have lysing ability to the red blood cell membrane.

5. The reagent of claim 4,
   wherein the nonionic surfactant is selected from the group consisting of polyoxyethylene sorbitan monoisostearate, polyoxyethylene sorbitan monooleate, polyoxyethylene hydrogenated castor oil, polyoxyethylene phytosterol, polyoxyethylene phytostanol, polyoxyethylene laurylether, polyoxyethylene oreylether, polyoxyethylene polyoxypropylene decyltetradecylether, polyoxyethylene polyoxypropylene cetylether, and polyoxyethylene monolaurate.

6. The reagent of claim 1, comprising a pH adjusting agent for adjusting pH of the reagent.

7. The reagent of claim 6, having pH of 5 to 7.

8. The reagent of claim 1, wherein the fluorescent dye comprises bisbenzimide type fluorescent dye which is preferential for DNA over RNA.

9. The reagent of claim 8, wherein the bisbenzimide type fluorescent dye has the following chemical formula

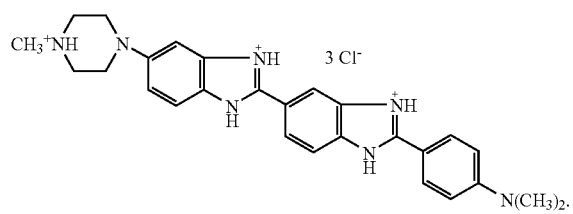

* * * * *